US008563520B2

(12) United States Patent
Saragovi

(10) Patent No.: US 8,563,520 B2
(45) Date of Patent: Oct. 22, 2013

(54) TREATMENT OF OCULAR DISEASE WITH INHIBITORS OF ALPHA2 MACROGLOBULIN PROTEIN

(75) Inventor: H. Uri Saragovi, Montreal (CA)

(73) Assignee: McGill University (CA)

(*) Notice: Subject to any disclaimer, the term of this patent is extended or adjusted under 35 U.S.C. 154(b) by 626 days.

(21) Appl. No.: 12/154,396

(22) Filed: May 22, 2008

(65) Prior Publication Data

US 2008/0305103 A1    Dec. 11, 2008

Related U.S. Application Data

(63) Continuation-in-part of application No. PCT/US2006/045169, filed on Nov. 22, 2006.

(60) Provisional application No. 60/739,570, filed on Nov. 22, 2005.

(51) Int. Cl.
*A61K 39/395*    (2006.01)
*A61K 47/06*    (2006.01)

(52) U.S. Cl.
USPC .................. 514/20.8; 424/145.1; 424/130.1

(58) Field of Classification Search
None
See application file for complete search history.

(56) References Cited

U.S. PATENT DOCUMENTS

| 4,911,920 A | 3/1990 | Jani et al. |
| 6,441,047 B2 * | 8/2002 | DeSantis, Jr. |
| 6,482,854 B1 * | 11/2002 | Lipton et al. |
| 2009/0318335 A1 | 12/2009 | Vitagliano et al. |

FOREIGN PATENT DOCUMENTS

| WO | WO 2007/062101 A2 | 5/2007 |
| WO | WO2007062101 A3 * | 5/2007 |
| WO | 2008056217 A1 | 5/2008 |

OTHER PUBLICATIONS

Lipton, S.A., Failures and successes of NMDA receptor antagonists: molecular basis for the use of open-channel blockers like memantine in the treatment of acute and chronic neurologic insults, J. Am. Soc. Exp. Neurother. 1:101-110, Jan. 2004.*
Morrison et al. Statistical analysis of retinal gene expression following chronic IOP evaluation using cDNA microarray, Invest. Opthal. Vis. Sci. 46 E-abstract 1250, May 2005.*
Luna et al., Differential protein expression of LRP and receptor-associated ligands in neovascular rat retinals and patients with neovascular eye disease, ARVO Annual Meeting Abstract Search and Program Planner, vol. 2003, pp. Abstract No. 3576, May 2003.*
Chidlow et al., Pharmacological neuroprotection for glaucoma, Drugs, 67(5):725-759, 2007.*
Vasudevan et al., Neurprotection in glaucoma, Indian J. Ophthalmol. 59(Suppl 1):S102-S113, Jan. 2011.*

Ahmed, F., et al., "Microarray Analysis of Changes in mRNA Levels in the Rat Retina after Experimental Elevation of Intraocular Pressure," *Invest. Ophthalmol. Vis. Sci.*, 45(4): 1247-1258 (2004).
Bacskai, B.J., et al., "The Endocytic Receptor Protein LRP also Mediates Neuronal Calcium Signaling via N-methyl-d-aspartate Receptors," *Proc. Natl. Acad. Sci. USA*, 97(21): 11551-11556 (2000).
Berkelaar, M., et al., "Axotomy Results in Delayed Death and Apoptosis of Retinal Ganglion Cells in Adult Rats," *J. Neurosci.*, 14(7): 4368-4374 (1994).
Birkenmeier, G., et al., "Epitope Mapping by Screening of Phage Display Libraries of a Monoclonal Antibody Directed Against the Receptor Binding Domain of Human α2-Macroglobulin," *Federation of European Biochemical Societies Letters*, 416: 193-196 (1997).
Birkenmeier, G., et al., "Immunocytochemical Demonstration of Alpha 2-M-R/LRP on Müller (glial) cells isolated from Rabbit and Human Retina," *Neuroreport.*, 8(1): 149-151 (1996).
Chiabrando, G.A., et al., "Low-Density Lipoprotein Receptor-Related Protein Mediates in PC12 Cell Cultures the Inhibition of Nerve Growth Factor-Promoted Neurite Outgrowth by Pregnancy Zone Protein and α2-Macroglobulin," *J Neurosci. Res.*, 70(1): 57-64 (2002).
Connor, M., and Christie, M.D., "Opioid Receptor Signalling Mechanisms," *Clin. Exp. Pharmacol. Physiol.*, 26(7): 493-499 (1999).
Database Biosis Biosciences Information Service, Philadelphia, PA, US; ARVO Ann. Meeting Abst. Search & Program Planner 2003, Luna, J.D., et al., "Differential protein expression of LRP and receptor-associated ligands in neovascular rat retinas and patients with neovascular eye disease," Database accession No. PREV200300551452.
Di Paolo, G., et al., "Decreased Synaptic Vesicle Recycling Efficiency and Cognitive Deficits in Amphiphysin 1 Knockout Mice," *Neuron*, 33: 789-804 (2002).

(Continued)

*Primary Examiner* — Claire Kaufman
(74) *Attorney, Agent, or Firm* — Pillsbury Winthrop Shaw Pittman LLP

(57) ABSTRACT

The present invention relates to methods to treat glaucoma and glaucoma-related conditions through the regulation of changes in gene expression that are mediated by high intraocular pressure or α2 macroglobulin administration. Glaucoma, retinal ganglion cell (RGC) death and chronic ocular hypertension are treated using pharmaceutical compositions which comprise substances that inhibit the expression or activity of intraocular pressure-regulated early genes (IP-REGs) or their gene products that are up-regulated by high intraocular pressure or α2 macroglobulin administration and/or which increase the expression or activity of IPREGs or their gene products that are down-regulated by high intraocular pressure or α2 macroglobulin administration. The invention also relates to methods of identifying an IPREG and methods to test for chronic ocular degeneration and the onset of RGC stress in an individual by measuring the expression level of IPREG proteins.

12 Claims, 9 Drawing Sheets
(1 of 9 Drawing Sheet(s) Filed in Color)

(56) References Cited

OTHER PUBLICATIONS

Di Paolo, A., et al., "Prolonged Delivery of Brain-Derived Neurotrophic Factor by Adenovirus-Infected Müller Cells Temporarily Rescues Injured Retinal Ganglion Cells," *Proc. Natl. Acad. Sci. USA*, 95: 3978-3983 (1998).
Esson, D.W., et al., "Microarray Analysis of the Failure of Filtering Blebs in a Rat Model of Glaucoma Filtering Surgery," *Invest. Ophthalmol. Vis. Sci.*, 45(12): 4450-4462 (2004).
Ferrani-Kile, K. and Leslie, S.W., "Modulation of Protein Tyrosine Phosphatase Activity Alters the Subunit Assembly in Native N-Methyl-D-aspartate Receptor Complex,"*J.Pharmacol. Exp. Ther.*, 314(1): 86-93 (2005).
Hashimoto, Y., et al., "Neuronal Apoptosis by Apolipoprotein E4 through Low-Density Lipoprotein Receptor-Related Protein and Heterotrimeric GTPases," *J. Neurosci.*, 20(22): 8401-8409 (2000).
Herz, J., "LRP: a Bright Beacon at the Blood-Brain Barrier," *J. Clin. Invest.*, 112(10): 1483-1485 (2003).
Hosoya, O., et al., "Localized Expression of Amphiphysin 1r, a Retina-Specific Variant of Amphipysic 1, in the Ribbon Synapse and its Functional Implication," *Eur. J. Neurosci.*, 19(8): 2179-2187 (2004).
Hou, X.Y., et al., "Activation of NMDA Receptors and L-type Voltage-Gated Calcium Channels Mediates Enhanced Formation of Fyn-PSD95-NR2a Complex After Transient Brain Ischemia," *Brain Res.*, 955(1-2): 123-132 (2002).
Hou, X.Y., et al., "Suppression of Postsynaptic Density Protein 95 by Antisense Oligonucleotides Diminishes Postischemic Pyramidal Cell Death in Rat Hippocampal CA1 Subfield," *Neurosci. Lett.*, 385(3): 230-233 (2005).
Howard, M.T., et al., "Disruption of a Topoisomerase-DNA Cleavage Complex by a DNA Helicase," *Proc. Natl. Acad. Sci. USA*, 91: 12031-12035 (1994).
Johanson, S.O., et al., "Signal Transduction from Membrane to Nucleus: the Special Case for Neurons," *Neurochem. Res.*, 21(7): 779-785 (1996).
Kan C. C., et al., "Nucleotide Sequence of cDNA Encoding Human $\alpha_2$-Macroglobulin and Assignment of the Chromosomal Locus," *Proc. Natl. Acad. Sci. USA*, 82(8): 2282-2286 (1985).
Kass, MA, et al., "Topical Timolol Administration Reduces the Incidence of Glaucomatous Damage in Ocular Hypertensive Individuals. A Randomized, Double-Masked, Long-Term Clinical Trial," *Arch. Ophthalmol.*, 107(11): 1590-1598 (1989).
Kelleher, K.L., et al., "Developmental Expression of Messenger RNA Levels of the Alpha Subunit of the GTP-Binding Protein, Gz, in the Mouse Nervous System," *Brain. Res. Dev. Brain. Res.*, 107(2): 247-253 (1998).
Lei, G., et al., "Gain Control of N-methyl-D-aspartate Receptor Activity by Receptor-Like Protein Tyrosine Phosphate $\alpha$," *EMBO J.*, 21(12): 2977-2989 (2002).
Lopes, M.B.S., et al., "Expression of $\alpha_2$-Macroglobulin Receptor/ low Density Lipoprotein Receptor-Related Protein is Increased in Reactive and Neoplastic Glial Cells," *FEBS Lett.*, 338: 301-305 (1994).
Matthijs, G., et al., "Structure of the Human Alpha-2 Macroglobulin Gene and its Promotor," *Biochem. Biophys.Res. Commun.*, 184(2): 596-603 (1992).
Meng, J. and Casey, P.J., "Activation of $G_z$ Attenuates Rap1-mediated Differentiation of PC12 Cells," *J. Biol. Chem.*, 277(45): 43417-43424 (2002).
O'Brien, C., et al., "Intraocular Pressure and the Rate of Visual Field Loss in Chronic Open-Angle Glaucoma," *Am. J. Ophthalmol.*, 111(4): 491-500 (1991).
Pang, I-H, et al., "Evaluation of Inducible Nitric Oxide Synthase in Glaucomatous Optic Neuropathy and Pressure-Induced Optic Nerve Damage," *Invest. Ophthalmol. Vis. Sci.*, 46(4): 1313-1321 (2005).
Qiu, Z., "ApoE Isoforms Affect Neuronal N-Methyl-D-Aspartate Calcium Responses and Toxicity Via Receptor-Mediated Processes," *Neuroscience*, 122(2): 291-303 (2003).
Qiu, Z., et al., "Apolipoprotein E Receptors Mediate Neurite Outgrowth through Activation of p44/42 Mitogen-Activated Protein Kinase in Primary Neurons," *J. Biol. Chem.*, 279(33): 34948-34956 (2004).
Qui, Z., et al., "$\alpha_2$-Macroglobulin Exposure Reduces Calcium Responses to N-Methyl-D-Aspartate via Low Density Lipoprotein Receptor-Related Protein in Cultured Hippocampal Neurons," *J. Biol. Chem.*, 277(17): 14458-14466 (2002).
Rudzinski, M., et al., "Changes in Retinal Expression of Neurotrophins and Neurotrophin Receptors Induced by Ocular Hypertension," *J. Neurobiol.*, 58(3): 341-354 (2004).
Schlötzer-Schrehardt, U., et al., "Matrix Metalloproteinases and their Inhibitors in Aqueous Humor of Patients with Pseudoexfoliation Syndrome/Glaucoma and Primary Open-Angle Glaucoma," *Invest. Ophthalmol. Vis. Sci.*, 44(3): 1117-1125 (2003).
Skornicka, E.L., et al., "Comparative Binding of Biotinylated Neurotrophins to Alpha (2)-Macroglobulin Family of Proteins: Relationship Between Cytokine-Binding and Neuro-Modulatory Activities of the Macroglobulins," *J. Neurosci. Res.*, 67(3): 346-353 (2002).
Szatmari, E., et al., "A Positive Feedback Loop between Glycogen Synthase Kinase 3β and Protein Phosphatase 1 after Stimulation of NR2B NMDA Receptors in Forebrain Neurons," *J. Biol. Chem.*, 280(45): 37526-37535 (2005).
Tomizawa, K., et al., "Cophosphorylation of Amphiphysin I and Dynamin I by Cdk5 Regulates Clathrin-Mediated Endocytosis of Synaptic Vesicles," *J. Cell Biol.*, 163(4): 813-824 (2003).
Tsutsui, K., et al. "Involvement of DNA Topoisomerase IIβ in Neuronal Differentiation," *J. Biol. Chem.*, 276(8): 5769-5778 (2001).
van Zundert, B., et al., "Receptor Compartmentalization and Trafficking at Glutamate Synapses: a Developmental Proposal," *Trends Neurosci.*, 27(7): 428-437 (2004).
Vittitow, J. and Borrast T., "Genes expressed in the human trabecular meshwork during pressure-induced homeostatic response," *J. Cell. Physiol.*, 201: 126-137 (2004).
Wax, M. and Patil, R., "A Rationale for Gene Targeting in Glaucoma Therapy," *J. Ocul. Pharmacol.*, 10(1): 403-410 (1994).
Wechsler, A. and Teichberg, V.I., "Brain Spectrin Binding to the NMDA Receptor is Regulated by Phosporylation, Calcium and Calmodulin," *EMBO J.*, 17(14): 3931-3939 (1998).
White, A.R., et al., "Contrasting, Species-Dependent Modulation of Copper-Mediated Neurotoxicity by the Alzheimer's Disease Amyloid Precursor Protein," *J. Neurosci.*, 22(2): 365-376 (2002).
Yepes, M., et al., "Tissue-Type Plasminogen Activator Induces Opening of the Blood-Brain Barrier via the LDL Receptor-Related Protein," *J. Clin. Invest.*, 112(10): 1533-1540 (2003).
Tsai, J.C. and Kanner, E.M., "Current and Emerging Medical Therapies for Glaucoma," *Expert Opin. Emerging Drugs*, 10(1): 109-118 (2005).
Database Biosis Biosciences Information Service, Philadelphia, PA, US; Nippon Ganka Gakkai Zasshi 101(3) p. 265-271 1997, Fukuchi Takeo, et al., "Expression of proteinase inhibitors in the human trabecular meshwork," Database accession No. PREV199799557740.
Notification of Transmittal of the International Search Report and the Written Opinion of the International Searching Authority, or the Declaration, International Application No. PCT/US2006/045169, Date of Mailing Jan. 16, 2008.
Notification Concerning Transmittal of International Preliminary Report on Patentability (Chapter 1 of the Patent Cooperation Treaty), International Application No. PCT/US2006/045169, Date of Mailing Jun. 5, 2008.
European Examination Report, European Application No. 06 844 496.7, Dated Mar. 13, 2009.
Colangelo, A.M., A New Nerve Growth Factor-Mimetic Peptide Active on Neuropathic Pain in Rats, 2008, J. of Neuroscience, 28(11):2698-2709.
Ando, H., et al., MMPs and Proteinase Inhibitors in the Human Aqueous Humor, Investigative Ophthalmology & Visual Science, 1993, 34(13):3541-3548.
Yu, T.C., et al., Comparative Study of Native Proteins in Aqueous Humor and Serum-Detection of Characteristic Aqueous Humor Proteins, Japanese Journal of Ophthalmology, 1987, 31(2):235-348.

(56) References Cited

OTHER PUBLICATIONS

Lerche, R.C., et al., Incidence of Hyperviscosity Conditions in Patients Suffering From Retinal Vascular Occlusion, ARVO Annual Meeting Abstract Search and Program Planner [online], 2002, Abstract No. 492 [retrieved on Mar. 12, 2012]. Retrieved from the internet <URL: http://abstracts.iovs.org//cgi/content/abstract/43/12/492?sid+c3e80506-ebbb-4d4d-9e0d-4b5ec3085638>.

Milenkovic, I., et al., Effect of alpha2-macroglubulin on Retinal Glial Cell Proliferation, Graefe's Archive for Clinical and Experimental Ophthalmology, 2005, 243(8):811-816.

* cited by examiner

A.

B.

G = Glaucoma
C = Cataract

Venn Diagram Outlining the number of Common Genes at Day 3 (pink), Day 7 (blue), and Day 14 (green).

TREATMENT OF OCULAR DISEASE WITH INHIBITORS OF ALPHA2 MACROGLOBULIN PROTEIN

RELATED APPLICATIONS

This application is a continuation-in-part of International Application No. PCT/US2006/045169, which designated the United States and was filed on Nov. 22, 2006, published in English, which claims the benefit of U.S. Provisional Application No. 60/739,570, filed on Nov. 22, 2005. The entire teachings of the above applications are incorporated herein by reference.

BACKGROUND OF THE INVENTION

Glaucoma impairs the vision of millions people worldwide and is one of the leading causes of blindness. Accounting for a significant number of patient visits to ophthalmologists' offices in North America, hundreds of thousands of new cases of glaucoma are diagnosed in the United States each year with many of those cases afflicting those of the older population. In fact, the annual cost of glaucoma has reached billions of dollars in the United States alone.

In open angle glaucoma, the most frequent form of glaucoma, visual field loss is caused by progressive optic nerve fiber deterioration due to the death of retinal neurons. Those retinal neurons, called retinal ganglion cells (RGCs), make up the inner retinal cell layers of the optic nerve. Concomitant with the progressive death of RGCs is an elevation of intraocular pressure (IOP) in the eye. This ocular hypertension is detected in the majority of glaucoma patients at some point in the disease.

It is believed that exposure to high IOP induces the chronic and progressive apoptotic death of RGCs at a constant weekly rate. Thus, glaucoma is a slow, chronic, and progressive neurodegenerative disease of RGCs. The IOP of those with glaucoma measures, on average, at levels that are 1.4 to 1.7 fold higher than the IOP of those without glaucoma. However, glaucoma is difficult to treat because the exact onset of high IOP is unpredictable and generally unapparent until peripheral vision loss occurs, at which point irreversible RGC loss is often advanced. Thus, glaucoma is primarily indolent with peripheral loss of vision generally only becoming clinically evident when most of the optic nerve axons are lost.

The mainstream treatment for glaucoma is the pharmacological reduction of high IOP back to near normal IOP levels. However, despite the normalization of IOP, sustained RGC death and clinical evolution towards glaucoma often continue, which suggests that high IOP may not be the direct cause of RGC apoptosis. Thus, exactly how ocular hypertension leads to the triggering of biochemical events that result in RGC apoptosis is unknown.

Current mechanisms proposed for RGC apoptosis in glaucoma include (i) excitotoxic damage (hyperactive NMDA receptors, elevated glutamate, $Ca^{++}$ fluxes, and nitric oxide) (ii) ischemic or mechanical retinal injury leading to activation of microglia and macrophages which cause bystander damage of neighboring retinal cells and (iii) mechanical compression of the optic nerve head preventing axonal transport required for RGC survival (also known as "cuffing" or "physiologic axotomy"). However, these mechanisms alone can not explain why only RGCs should be susceptible to apoptosis instead of all cells in the inner retinal layer that are exposed to the potentially deleterious effects of altered glutamate/nitric oxide/$Ca^{++}$ and to mechanical stress. Neither do these hypotheses explain why the normalization of IOP does not result in the complete arrest of RGC death when axonal transport is restored.

Thus, although high IOP is clearly correlated with RGC death in glaucoma, virtually no links have been made at the molecular level between high IOP and RGC apoptosis. As current glaucoma therapies which reduce IOP often do not prevent continued loss of RGC cells and deterioration of the optic nerve, what is needed are therapies that treat the molecular causes of glaucoma progression.

SUMMARY OF THE INVENTION

The present invention relates to a method of treating glaucoma in a mammal. Several genes having altered expression induced by high IOP and functionally relevant to cell signaling and cell death have been identified. These genes, some having increased and others reduced expression, have been termed intraocular pressure-regulated early genes or IPREGs and include: α2 macroglobulin, PSD-95/SAP90-associated protein-4, Reggie1-1, RBCK, Gzα, Protein phosphatase 1 gamma, Ribosomal protein L23-related product, Gial fibrillary acidic protein, Cyclic nucleotide-gated cation channel, SPARC, B-2 arylamine N-acetyltransferase, Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase, Asparagine synthase and several cDNA clones and expressed sequence tags (ESTs). Since the neurotoxic effects of α2 macroglobulin protein can cause glaucomatous-like RGC loss, several genes having altered expression induced by administration of α2 macroglobulin protein have been identified. These genes can exhibit upregulation, downregulation or a combination of upregulation and downregulation depending on the time post-administration of the α2 macroglobulin protein. In addition, for purposes of the invention described herein, these α2 macroglobulin regulated genes are also referred to as IPREGS.

The IPREGs listed in Tables 4 and 5 are examples of IPREGS having altered expression induced by administration of α2 macroglobulin protein. In a particular embodiment, the IPREGs having altered expression induced by administration of α2 macroglobulin protein are the genes listed in Table 6. In a more particular embodiment, the IPREGs are beta A2 crystallin, beta B1 crystallin, beta B2 crystallin and beta B3 crystallin. It is understood that certain IPREGs identified herein can be altered by both high IOP and α2 macroglobulin protein.

In one embodiment, the invention relates to a method of treating glaucoma in a mammal by administering to the mammal an effective amount of a composition that inhibits the expression or activity of one or more up-regulated IPREGs. In one embodiment, the up-regulated IPREGs are selected from the group consisting of α2 macroglobulin, PSD-95/SAP90-associated protein-4, Reggie1-1, RBCK, Gzα, Protein phosphatase 1 gamma, Ribosomal protein L23-related product, Gial fibrillary acidic protein, Cyclic nucleotide-gated cation channel, SPARC and B-2 arylamine N-acetyltransferase. In another embodiment, the inhibitory composition comprises one or more from the group consisting of small interfering RNAs (siRNAs), antisense oligonucleotides, neutralizing antibodies, small molecules, recombinant gene expression vectors, recombinant gene viral vectors, synthetic peptides, recombinant polypeptides, peptidomimetics and inhibitors of the regulatory regions of the IPREGs. In yet another embodiment, the composition is administered by intraocular injection, topical conjunctival application, topical corneal application or a mechanical delivery device. In another embodiment, the method further comprises administering an intraocular pressure-normalizing drug, selected from the group consisting of non-selective-adrenoceptor blockers, selective-adrenoceptor blockers, prostaglandins, carbonic anhydrase inhibitors, adrenergic agonists and miotics.

The present invention also relates to a method of treating glaucoma in a mammal by administering to the mammal an effective amount of a composition that increases the expression or activity of one or more down-regulated IPREGs. In one embodiment, the down-regulated IPREGs whose expression is increased are one or more selected from the group consisting of Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase and Asparagine synthase. The composition is comprised of one or more substances that increase the expression or activity of down-regulated IPREGs and can be administered by the aforementioned routes and can be further administered in combination with an intraocular pressure-normalizing drug.

In another embodiment, the invention relates to a method of treating glaucoma in a mammal by administering to the mammal an effective amount of a composition that regulates (i.e., increases down regulated genes and decreases up regulated genes) the expression of one or more of the IPREGs listed in Tables 4 and 5. In a particular embodiment, the IPREGs are one or more genes selected from the genes listed in Table 6. In a further embodiment, the IPREGs are one or more genes selected from beta A2 crystallin, beta B1 crystallin, beta B2 crystallin and beta B3 crystallin.

The present invention also relates to treating glaucoma in a mammal by administering an effective amount of a composition that both inhibits the expression or activity of at least one up-regulated IPREG and increases the expression or activity of at least one down-regulated IPREG. The composition regulates the identified IPREGs using substances that inhibit the expression or activity (for up-regulated IPREGs) and increase the expression or activity (for down-regulated IPREGs) of the IPREGs. The IPREGs having altered expression include those having altered expression induced by high IOP, those having altered expression induced by administration of α2 macroglobulin protein and those having altered expression induced by both.

The invention further relates to a method of preventing RGC death mediated by high IOP comprising administering to an individual an effective amount of an IPREG-regulating composition such that the composition inhibits the expression or activity of one or more up-regulated IPREGs and/or increases the expression or activity of one or more down-regulated IPREGs. The IPREGs having altered expression include those having altered expression induced by high IOP, those having altered expression induced by administration of α2 macroglobulin protein and those having altered expression induced by both.

In addition, the invention relates to a method of preventing chronic ocular degeneration in a mammal comprising administering to the mammal an effective amount an IPREG-regulating composition, such that the composition inhibits the expression or activity of one or more up-regulated IPREGs and/or increases the expression or activity of one or more down-regulated IPREGs. The IPREGs having altered expression include those having altered expression induced by high IOP, those having altered expression induced by administration of α2 macroglobulin protein and those having altered expression induced by both.

The present invention also relates to a method of testing for chronic ocular degeneration in a patient comprising measuring the expression level of one or more IPREG proteins in the aqueous humor of the patient and comparing the expression level measured to that of the same one or more IPREG proteins in individuals with normal ocular function. A higher expression level of one or more up-regulated IPREG proteins and/or a lower expression level of one or more down-regulated IPREG proteins as compared to the expression of the same IPREG proteins in individuals with normal ocular function indicates that the patient has chronic ocular degeneration. The IPREGs having altered expression include those having altered expression induced by high IOP, those having altered expression induced by administration of α2 macroglobulin protein and those having altered expression induced by both.

The invention further relates to a method of testing for the onset of RGC stress in a patient comprising measuring the expression level of one or more IPREG proteins in the aqueous humor of the patient at an initial time point, measuring the expression level of the same one or more IPREG proteins in the aqueous humor of the patient at a later time point and comparing the expression level of the one or more IPREG proteins measured at the initial time point to that measured at the later time point such that a higher expression level of the one or more up-regulated IPREG proteins and/or a lower expression level of one or more down-regulated IPREG proteins in the patient indicates the onset of RGC stress in the patient.

A method is also provided for the identification of an intraocular pressure-regulated early gene (IRPEG), the method comprising determining whether expression of a gene is altered by ocular hypertension, wherein expression of the gene is not altered by retinal ganglion cell (RGC) damage. The method further comprises determining whether expression of the gene is altered early after the onset of ocular hypertension, determining whether the altered expression of the gene is sustained after onset of ocular hypertension or glaucoma and determining whether expression of the gene remains altered after ocular hypertension is reduced. In a particular embodiment, the role of the identified gene in RGC death and/or glaucoma is validated. The invention further relates to an IPREG identified by the aforementioned method.

The present invention also relates to pharmaceutical compositions used to treat glaucoma, chronic ocular degeneration or RGC death. Thus, the present invention relates to a pharmaceutical composition comprising an effective amount of at least one substance that inhibits the expression or activity of up-regulated IPREGs and a pharmaceutically acceptable carrier, wherein the composition is administered to treat glaucoma. In another embodiment, the pharmaceutical composition is administered to treat chronic ocular degeneration or RGC death. In addition, the invention also relates to a pharmaceutical composition comprising an effective amount of at least one substance that increases the expression or activity of down-regulated IPREGs and a pharmaceutically acceptable carrier wherein the composition is administered to treat glaucoma or, in a further embodiment, chronic ocular degeneration or RGC death. The invention further relates to a pharmaceutical composition that comprises an effective amount of at least one substance that inhibits the expression or activity of up-regulated IPREGs and at least one substance that increases the expression or activity of down-regulated IPREGs and an acceptable pharmaceutical carrier, wherein the composition is administered to treat glaucoma, chronic ocular degeneration or RGC death. The IPREGs having altered expression include those having altered expression induced by high IOP, those having altered expression induced by administration of α2 macroglobulin protein and those having altered expression induced by both.

A method is also provided for the identification of a compound which regulates IPREGs having altered expression induced by high IOP, by administration of α2 macroglobulin protein or induced by both high IOP and administration of α2 macroglobulin protein. The method comprises contacting a cell having aberrant expression of an IPREG with a test compound and determining whether the test compound regulates expression of the IPREG. In one embodiment, the expression of the IPREG is down regulated. In another embodiment, the expression of the IPREG is upregulated.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments of the invention. The drawings are not necessarily to scale, emphasis instead being placed upon illustrating embodiments of the present invention.

FIG. 1 panel B is a graph illustrating the loss of retinal ganglion cells in a mouse model of ocular hypertension with and without betaxolol treatment. (B) Progressive loss of RGCs triggered by short-term ocular hypertension. Normalization of IOP with betaxolol (from day ~7 onwards) reduces the rate of RGC loss, but does not prevent it.

DETAILED DESCRIPTION OF THE INVENTION

Figure 1:
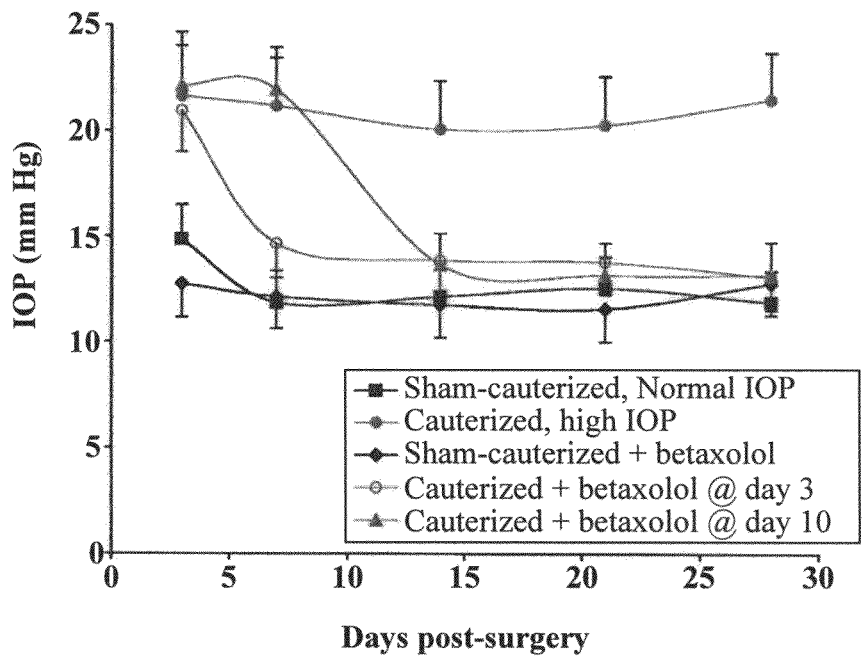
FIG. 1 panel A is a graph illustrating the change in intraocular pressure in treatment of a mouse model of ocular hypertension with betaxolol. (A) Mean IOP values±s.d., n=4-6. At day 0 eyes were surgically cauterized or were left normal. At days 3 or 10 the indicated groups were treated with a β-blocker (betaxolol 0.5%, Alcon Labs), the other groups were untreated. Daily treatment with β-blocker continued until day 28.
Figure 1:
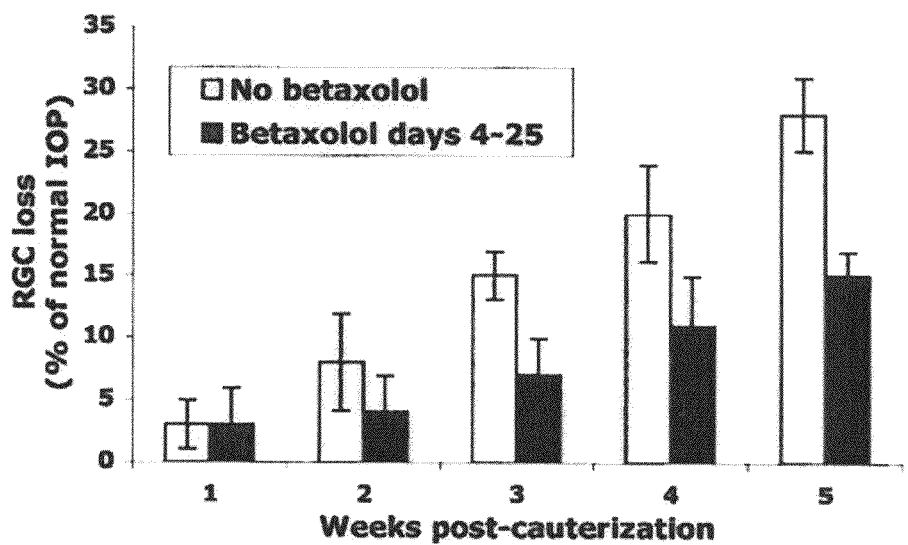

The present invention generally relates to methods of treating and diagnosing glaucoma in a mammal by regulating the aberrant expression and/or function/activity of genes triggered by ocular hypertension which are also likely involved in RGC apoptosis or genes whose expression is altered by α2 macroglobulin administration. As used herein, the term "intraocular pressure-regulated early gene" or "IPREG" describes a gene that meets one or more criteria that implicate the gene in ocular degeneration. One criteria is that any molecular changes to a candidate gene and/or gene product be induced by high IOP, rather than arise as the result of RGC damage. Another criteria is that these molecular changes be triggered relatively early after the onset of high IOP. In addition, it would be preferable that any molecular changes to the gene and/or gene product triggered by high IOP be sustained or long-lived even after IOP has been normalized. In a particularly preferred aspect, molecular changes to the gene and/ or gene product would sensitize or prime RGCs for death, in other words, the genes would have a direct or indirect role in the transduction of death signals (e.g., up-regulated gene products) or neuroprotection (e.g., down-regulated gene products). Another criteria is that altered expression of the genes occur due to α2 macroglobulin protein administration.

Gene Identification

Genes differentially expressed under conditions of high IOP or α2 macroglobulin administration can be identified by several methods known in the art including differential display, gene array chip, proteomics and genomics and, in a particular embodiment, a gene array chip is used. The methods of using gene array systems are well-known in the art but, briefly, mRNA from a tissue of interest (e.g., retina) can be isolated and prepared from a source of the tissue that is normal (i.e., a control source) and a source of the tissue that is of interest (e.g., abnormal or diseased tissue). cDNAs are made from the isolated mRNA and labeled cRNA probes made from the purified cDNAs, which are then incubated with a gene array DNA chip under hybridizing conditions. Genes on the chip to which the probes have specifically bound can be identified by the detection of whatever label is associated with the cRNA probes and an analysis done to measure the fold changes in gene expression between the gene array chip hybridized with cRNA probes from normal tissue and the gene array chip hybridized with cRNA from the tissue of interest. Generally, a statistical analysis is performed to determine whether the changes in gene expression observed between the chips are significant and those changes in gene expression deemed significant then validated in the tissues themselves (e.g., by RT-PCR, northern blot, immunoblot or immunofluorescence).

In the case of the present invention, the source of retinal mRNA can be from any system capable of undergoing and/or duplicating the changes seen in glaucoma, i.e., high IOP, RGC death and sustained RGC death after normalization of high IOP; thus, the mRNA source can be from human tissues, experimental animal models or cell/tissue culture systems. In the case of the present invention, an episcleral vein cauterization rat model of ocular hypertension was employed and mRNA isolated from the dissected retinas of rats that were normal, rats altered to have high IOP and rats altered to have high IOP that was subsequently pharmacologically normalized. Thirty-three genes and expressed sequence tags (ESTs) were identified that had significantly altered expression after induction of high IOP. All of the genes were candidates of interest in terms of understanding the causes of RGC damage and nine of the identified genes retained significantly altered expression 21 days after the pharmacological normalization of high IOP in the rat model.

Intraocular Pressure-Regulated Early Genes

Several genes were identified that had altered expression in the retina after induction of high IOP and after α2 macroglobulin protein administration. Genes found to have up-regulated expression in the analysis due to induction of high IOP were: α2 macroglobulin, PSD-95/SAP90-associated protein-4, Reggie1-1, RBCK, Gzα, Protein phosphatase 1 gamma, Ribosomal protein L23-related product, Glial fibrillary acidic protein, Cyclic nucleotide-gated cation channel, SPARC and B-2 arylamine N-acetyltransferase while those exhibiting down-regulated expression included Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase and Asparagine synthase. The altered expression seen for many of the genes is consistent with postulated mechanisms of RGC death in glaucoma including glutamatergic stress, bystander effects, growth factor deprivation and reduced axonal growth. Genes found to have altered expression due to α2 macroglobulin administration were the genes listed in Tables 4 and 5. In a particular embodiment, genes found to have altered expression due to α2 macroglobulin administration were the genes listed in Table 6. In a more particular embodiment, genes found to have altered expression due to α2 macroglobulin administration were beta A2 crystallin, beta B1 crystallin, beta B2 crystallin and beta B3 crystallin.

For example, one IPREG identified with up-regulated expression, α2 macroglobulin, binds its receptor LRP-1, resulting in increased intracellular $Ca^{2+}$ through activation of NMDA receptors. Interestingly, NMDA receptor activity has been linked to neural apoptosis. In addition, α2 macroglobulin binds to and neutralizes retinal neurotrophins and, in particular, Nerve Growth Factor (NGF), which is an important survival factor for RGCs. Thus, overexpression of α2 macroglobulin could contribute to RGC death by exacerbating its effect on the excitatory activity of NMDA receptors to levels that are apoptotic and/or by decreasing the bioavailability of the survival factor NGF (see also FIG. 7).

The IPREG PSD95/SAP90 is also associated with NMDA receptors, binding the receptor C-terminus and inducing phosphorylation and activation of the receptor via the src-family kinases. The formation of a complex between the src-family kinase Fyn, PSD95 and NMDA receptors has been observed to enhance cell death in brain ischemia, whereas inhibition of PSD95 diminished post-ischemic neuronal cell death. Further, src family kinases that activate NMDA receptors are themselves activated by protein tyrosine phosphatases and, one src family phosphatase in particular, protein phosphatase 1 gamma (PP1), which is also an IPREG that was found to be up-regulated in the gene array analysis. PP1 is linked to RGC stress as it has been seen to inhibit axon regrowth in the injured adult CNS (see also FIG. 7).

In addition, another up-regulated IPREG, Gzα, is a direct interactor with and mediator of NMDA receptor signals through second messengers. In fact, Gzα has been reported to functionally potentiate α2 macroglobulin/LRP-1 receptor interaction with GTPases in a manner that exacerbates neuronal cell death. Thus, upregulation of the IPREGs α2 macroglobulin, PSD95, PP1 and Gzα illustrates what could be a coordination of signaling that contributes to RGC apoptosis through the enhanced activation of NMDA receptors.

Methods of Identifying an IPREG

Previous studies have identified genes having altered expression under high intraocular pressure conditions. (Ahmed F et al., *Invest Ophtalmol Vis Sci* 45:1247-1258, 2004; Esson D W et al., *Invest Ophtalmol Vis Sci* 45:4450-4462, 2004; Pang I H et al., *Invest Ophtalmol Vis Sci* 46:1313-1321, 2005). However, the change in expression of these genes does not account for the continued RGC death and subsequent loss of vision observed in patients even after the normalization of intraocular pressure. Thus, criteria were set to identify genes that are more likely implicated in ocular hypertension and/or maintenance of the RGC death that leads to the continued deterioration of the ocular condition in glaucoma. That is, those changes in retinal gene expression triggered by ocular hypertension and maintained after normalization of high IOP that causes RGC death. In addition, criteria were set to identify genes with altered expression due to α2 macroglobulin protein administration.

Accordingly, a method is provided for identifying intraocular pressure regulated genes (IPREGs) by determining whether one or more candidate genes meet some and preferably all of the specified criteria. The candidate genes to be evaluated using the method can be found/determined in a number of ways. For instance, one of skill in the art can simply select one or more genes of interest. Generally, selection of these candidate genes would be based on known expression of the genes in the eye (e.g., retinal cells) and some implication of the genes as being involved in, for example, regulation of cell activities/signaling (e.g., growth, differentiation, survival, adhesion), ocular hypertension and/or cell death. In addition, candidate genes can be chosen based on changes in gene expression due to some of the conditions outlined in the method. For example, the change in the expression of a gene or genes under conditions of high intraocular pressure, normalization of intraocular pressure, vision loss, retinal cell death, retinal cell survival and/or glaucoma in general. These changes in gene expression can be ascertained by comparing expression of the gene under the chosen condition(s) to a suitable control (e.g., normal and/or non-diseased conditions) using e.g., differential display or a gene microarray.

It is determined in the method whether expression of the candidate gene(s) is altered by ocular hypertension. However, expression of the gene is preferably specific to ocular hypertension and glaucoma, that is, its expression is not the result of the general RGC damage that may occur due to increased IOP. To determine if the alteration in the expression of the gene is altered simply due to RGC damage, expression of the gene(s) can be ascertained under general, preferably acute, conditions of RGC damage using other suitable experimental models (e.g., optic nerve axotomy rat model). It is also determined in the method whether expression of the gene is altered early after the onset of ocular hypertension. Thus, it is further ascertained whether altered expression of the gene or genes is due specifically to ocular hypertension, as opposed to later glaucoma-related events. The timeframe that is sufficiently early after the onset of ocular hypertension is dependent on a number of factors, including, for human patients, the patient population, the experimental animal model (e.g., mouse, rat, rabbit) or other model system (e.g., cell culture) and is best determined by the skilled artisan based on knowledge of the particular group, experimental animal model and/or other model system. For instance, in the model of ocular hypertension/glaucoma used herein, a rat episcleral vein cauterization model (see Example 1), early expression of genes after onset of ocular hypertension was between about 1 and 7 or about 3 and 7 days after induction of high IOP.

In another embodiment, it is determined in the method whether expression of the candidate gene(s) is altered by α2 macroglobulin protein administration.

The method further comprises determining whether expression of the candidate gene or genes is sustained/long-lived after onset of ocular hypertension or glaucoma. That is, it is determined whether expression of the gene remains altered after the early period following the onset of high IOP and is not, instead, a short-lived change in gene expression. This criteria makes it more likely that the genes identified are involved in maintaining ocular hypertension and the RGC death seen in glaucoma. The timeframe for the measurement of the expression of the gene(s) that meet this criteria is also dependent on the patient population or experimental model used. Generally, the expression of the gene(s) measured early after onset of high IOP, is compared to expression of the same gene(s) at some time point determined to be sufficiently later after onset of high IOP. In the rat episcleral vein cauterization model, the time point at which the sustained expression of genes having altered expression was measured at 28 days after cauterization of rat eyes (see Example 1, Group 2).

Identification of an IPREG further involves determining whether expression of the gene remains altered after ocular hypertension has been reduced and/or normalized, using, e.g., an intraocular pressure-regulating drug. This criteria better replicates the situation frequently seen in human patients in which continued visual field loss occurs despite the normalization of ocular hypertension and, thus, the criteria helps to ensure the identification of genes responsible for ocular degeneration in glaucoma. To evaluate genes having altered expression that is sustained after reduction of ocular hypertension, intraocular pressure can be reduced/normalized relatively soon after onset of high IOP. For instance, in the rat episcleral vein cauterization model, rats were treated with an intraocular pressure normalizing drug at day 3 post-cauterization (e.g., induction of high IOP), intraocular pressure seen to be normalized by day 7 post-cauterization and gene expression measured at day 28 post-cauterization, 21 days after normalization of high IOP (see also Example 1, Group 3). To determine whether gene expression is long-lived, the gene expression measured at the later time point after IOP reduction/normalization can be compared to gene expression early after onset of high IOP and/or normal gene expression (e.g., gene expression prior to onset/induction of ocular hypertension or that seen in normal individuals/animals).

Expression of the gene can be confirmed by other methods of measuring gene expression (e.g., northern blot, reverse-transcriptase PCR (traditional and real time), PCR) and, generally, are methods not used in elucidating altered expression in identification of the gene. In addition, a concomitant alteration in the expression of the gene product or protein can also to determined to confirm that changes in expression found at the transcript level are also found at the protein level. It may also be advantageous to determine for a particular protein/enzyme if changes in expression of the identified gene and/or protein results in changes in the protein's activity (e.g., kinase activity, binding activity, cleavage activity, protein activation or inhibition activity). Assessment of protein/enzyme activity can be done in a number of ways well-known in the art (e.g., spectrophotometric, fluorimetric, calorimetric, chemiluminescent, radiometric, chromatographic assays) and is dependent on the particular protein/enzyme.

After a gene has been identified as an IPREG by the method set forth above, the method can comprise other aspects to better understand the gene and its potential involvement in the regulation of and/or cause of RGC death and glaucoma progression. For candidate genes that are identified using a gene microarray, for example, determining the function and/or role of the identified gene in retina and in other cells/systems can be informative as to elucidating the putative role of the gene in glaucoma and RGC death. This information is available to one of skill in the art from numerous sources including the National Center for Biotechnology Information (NCBI) (e.g., PubMed (scientific articles), Entrez (genome, gene, protein), GenBank), other online searches, textbooks, theses, libraries, scientific presentations and the like. Of particular interest are identified genes thought and/or known to have a role in protecting cells from apoptosis or in inducing cellular apoptosis. Thus, the method can further comprise determining whether the gene is implicated in cell death or cell survival. Typically this can be done by researching the gene in one or more of the sources outlined above. Specifically, the up-regulation of identified genes implicated in cell death and the down-regulation of identified genes implicated in cell survival is consistent with their involvement in RGC death.

The method can also further comprise validating the role of the identified gene(s) in glaucoma in vivo. Ascertaining whether the identified gene(s) affects glaucoma, chronic ocular degeneration and/or RGC death in vivo can help validate that gene(s) as a viable target for glaucoma therapy. Accordingly the expression or activity of an up-regulated gene or gene product can be decreased in vivo or that of a down-regulated gene or gene product can be increased in vivo and the effect on RGC death (e.g., prevention), for example, determined. The level of change in the expression or activity of the identified gene or gene product that is necessary to ascertain a role of the gene or protein in glaucoma can be a level that demonstrates sufficient effect in preventing RGC death and/or glaucoma progression and this level can be determined by one of skill in the art. In one embodiment, the expression or activity of the gene or gene product is increased or decreased to normal levels (e.g., levels found in those animals not having ocular hypertension, RGC death and/or glaucoma). Decreasing (e.g., inhibiting) or increasing the expression or activity of the gene or gene product in vivo can be accomplished in a number of ways, as outlined below under *Methods of Treatment* (e.g., mutagenesis, small interfering (siRNA), antisense nucleotides, methylation/demethylation, neutralizing antibodies, dominant negative polypeptides, peptidomimetics). The effect of manipulation of the identified genes or proteins (e.g., back to normal levels) can be ascertained in one or more animal models (e.g., mouse, rat, rabbit, dog, monkey) and, if successful, ultimately in human patients.

The present invention also relates to an IPREG identified by the above methods. Thus, the identified IPREG fulfills the criteria specified in the method. Further, it can also be determined if the identified IPREG is implicated in cell death or cell survival. In a particular embodiment the role of the IPREG in RGC death and/or glaucoma is validated, generally by ascertaining if increasing or decreasing (reducing) the expression or activity of the identified IPREG to some level (e.g., normal levels) prevents RGC death and/or glaucoma progression.

Methods of Treatment

Accordingly, the present invention relates to methods of regulating aberrantly up-regulated and/or down-regulated genes that are implicated in glaucoma. The methods encompass those genes identified using the experimental model described above (i.e., an episcleral vein cauterization rat model of ocular hypertension), of known (e.g., α2 macroglobulin or Amphiphysin 1) and unknown (e.g., clone rx05013 or EST196604) function. The methods of the invention are used to treat a mammal and, in particular, a human. The above-mentioned animal model well-represents the characteristics of glaucoma seen in humans and is a good model for assessing the efficacy of treatment for glaucoma in a human being in vivo.

Thus, the present invention relates to a method of treating a mammal with glaucoma by administering an effective amount of a composition that inhibits the expression or activity of one or more up-regulated IPREGs. In particular, the method encompasses inhibiting one or more up-regulated genes identified in the gene array analysis. In one embodiment, these genes include: α2 macroglobulin, PSD-95/SAP90-associated protein-4, Reggie1-1, RBCK, Gzα, Protein phosphatase 1 gamma, Ribosomal protein L23-related product, Glial fibrillary acidic protein, Cyclic nucleotide-gated cation channel, SPARC and B-2 arylamine N-acetyltransferase.

As used herein, a composition or substance that inhibits the expression or activity of up-regulated IPREGs refers to a composition comprised of any substance that decreases the gene or expressed gene product(s) of the up-regulated IPREG (e.g., DNA, RNA or protein) and/or suppresses the functional activity of the up-regulated IPREG. Decreasing the expression level of an IPREG gene or gene product can be accomplished in a number of ways known to those with skill in the art including, for example: silencing of the IPREG (e.g., by inhibiting specific demethylases); targeted disruption of the positive transcriptional regulatory regions of the IPREG (e.g., by homologous recombination or mutagenesis); inhibition of the gene or gene products of positive transcriptional or translational regulators of the IPREG (e.g., using antisense oligonucleotides, small interfering RNAs, neutralizing antibodies, dominant negative genes/polypeptides, peptidomimetics); increasing the activity or expression of negative transcriptional or translational regulators of the IPREG (e.g., using recombinant gene expression vectors, recombinant viral vectors, synthetic peptides, recombinant polypeptides, hypermorphic genes/polypeptides) or inhibition of the IPREG itself (e.g., using antisense oligonucleotides, small interfering RNAs, neutralizing antibodies, dominant negative polypeptides, peptidomimetics). The functional activity of up-regulated IPREGs can be blocked in several ways including: direct inhibition of the activity of the IPREG protein (e.g., by using neutralizing antibodies, small molecules or peptidomimetics, dominant negative polypeptides); inhibition of genes and/or proteins that activate the IPREG (e.g., by blocking the expression or activity of the genes and/or proteins); activation of genes and/or proteins that inhibit the IPREG (e.g., by increasing the expression or activity of the genes and/or proteins); inhibition of genes and/or proteins that are downstream mediators of the IPREG function (e.g., by blocking the expression and/or activity of the mediator genes and/or proteins); introduction of genes and/or proteins that negatively regulate the IPREG (e.g., by using recombinant gene expression vectors, recombinant viral vectors or recombinant polypeptides); or gene replacement with, for instance, a hypomorphic mutant of the IPREG (e.g., by homologous recombination, overexpression using recombinant gene expression or viral vectors, or mutagenesis).

Thus, in one embodiment, the inhibitory composition can be directed to a protein which is a cellular receptor or a binding partner of an IPREG. For example, in one embodiment, the IPREG inhibited is α2 macroglobulin using, for instance, a neutralizing antibody to the protein. In another embodiment, α2 macroglobulin is inhibited by antagonization of its receptor (e.g., LRP-1) or antagonization of downstream mediators of α2 macroglobulin function (e.g., the IPREG Gzα and/or NMDA receptors) using, for example, an inhibitory peptide or peptidomimetic. Alternatively, a binding partner of α2 macroglobulin (e.g., NGF) can be inhibited, thereby blocking α2 macroglobulin function. Similarly, the inhibitory composition can be directed to the up-regulated IPREG, PSD-95, for instance, or genes and/or proteins (e.g., Fyn) that form a complex with PSD-95 to co-activate a receptor (e.g., the NMDA receptor) thereby mediating cell death. In another embodiment, the inhibitory composition could be directed to other downstream mediators of aα2 macroglobulin, Gzα and/or PSD-95 function, for example, the composition could inhibit the up-regulated IPREG PP1.

In one embodiment of the method, the composition administered to inhibit one or more up-regulated IPREGs can be comprised of small interfering RNAs, antisense oligonucleotides, neutralizing antibodies, small molecules, recombinant gene expression vectors, recombinant gene viral vectors, synthetic peptides, recombinant polypeptides, peptidomimetics or inhibitors of the regulatory regions of the IPREGs. As discussed previously, the substance of the composition can directly or indirectly inhibit IPREG expression, protein expression or functional activity. The composition can be administered in a suitable pharmaceutical carrier by one of several routes which include intraocular injection, topical conjunctival application, topical corneal application (e.g., eye drops, eye gels) or using a mechanical delivery device or eye inserts.

The present invention also relates to a method of treating glaucoma in a mammal by administering to the mammal an effective amount of a composition that increases the expression or activity of one or more down-regulated IPREGs. The method also encompasses increasing expression of those genes identified in the gene array analysis that are of known and unknown function and, in one embodiment of the method, the down-regulated genes are selected from the group consisting of: Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase and Asparagine synthase. In a particular embodiment, the IPREG whose expression or activity is increased is Amphiphysin 1.

As used herein, a composition or substance that increases the expression or activity of down-regulated IPREGs refers to a composition comprised of any substance that increases the gene or expressed gene product of the down-regulated IPREG or increases the active pool and/or activity of the down-regulated IPREG. Hence, the composition can be comprised of any substance that prevents silencing of the IPREG (e.g., by activating specific demethylases); disrupts negative transcriptional regulatory regions of the IPREG (e.g., by homologous recombination or mutagenesis); inhibits negative transcriptional or translational regulators of the IPREG or negative regulators of the IPREG's function (e.g., by using antisense oligonucleotides, small interfering RNAs or neutralizing antibodies); or increases the expression of positive transcriptional and/or translational regulators of the IPREG, positive regulators of the IPREG's function, the IPREG itself or its downstream mediators (e.g., by using recombinant gene expression vectors, recombinant viral vectors, synthetic peptides or recombinant polypeptides).

Accordingly, a composition that increases the expression or activity of down-regulated IPREGs can be comprised of one or more substances from the group consisting of small interfering RNAs, antisense oligonucleotides, neutralizing antibodies, small molecules, recombinant gene expression vectors, recombinant gene viral vectors, synthetic peptides, recombinant polypeptides, dominant negative genes or polypeptides, peptidomimetics and activators of the regulatory regions of the IPREGs. Hence, the composition can directly or indirectly increase down-regulated IPREG expression or functional activity.

The present invention also relates to methods of treating glaucoma or glaucoma-related problems by administering to a mammal a composition which regulates both up-regulated and down-regulated IPREGs. For example, the invention relates to a method of treating glaucoma in a mammal by administering to the mammal an effective amount of a composition that both inhibits the expression or activity of at least one up-regulated IPREG and increases the expression or activity of at least one down-regulated IPREG. The invention also relates to a method of preventing RGC death mediated by high IOP by administering to an individual an effective amount of a composition that regulates one or more IPREGs such that the composition inhibits the expression or activity of up-regulated IPREGs or increases the expression or activity of down-regulated IPREGs. Similarly, the invention further relates to a method of preventing ocular degeneration in a mammal by administering to the mammal an effective amount of a composition that regulates one or more IPREGs such that the composition inhibits the expression or activity of one or more IPREGs up-regulated in chronic ocular degeneration or increases the expression or activity of one or more IPREGs down-regulated in ocular degeneration.

In a further embodiment of the methods, the up-regulated IPREGs inhibited by the composition include those selected from the group consisting of α2 macroglobulin, PSD-95/SAP90-associated protein-4, Reggie1-1, RBCK, Gzα, Protein phosphatase 1 gamma, Ribosomal protein L23-related product, Glial fibrillary acidic protein, Cyclic nucleotide-gated cation channel, SPARC and B-2 arylamine N-acetyl-transferase and the down-regulated IPREGs whose expression is increased by the composition include those selected from the group consisting of Amyloid precursor-like protein 2, Amphiphysin 1, Crybb2, Ras-related p23, Helicase Rap 30, Proteosome rPA28 subunit beta, ATPase alpha-1 subunit, BetaA3/A1 crystallin, Beta A4 crystallin, S-adenosylmethionine synthase and Asparagine synthase.

The composition that regulates one or more IPREGs in the methods can be comprised of any substance that directly or indirectly increases the expression or function of the down-regulated IPREGs and/or inhibits the expression or function of the up-regulated IPREGs. Thus, in yet a further embodiment, the composition is comprised of small interfering RNAs, antisense oligonucleotides, neutralizing antibodies, small molecules, recombinant gene expression vectors, recombinant gene viral vectors and recombinant polypeptides, peptidomimetics, inhibitors of the regulatory regions of IPREGs and activators of the regulatory regions of IPREGs. The above composition is also preferably administered in a suitable pharmaceutical carrier by one of several routes including intraocular injection, topical conjunctival application, topical corneal application and using a mechanical delivery device.

Experimental testing of the effectiveness of inhibiting α2 macroglobulin (an up-regulated IPREG) in order to treat glaucoma indicated that RGC survival seen through the inhibition of α2 macroglobulin was enhanced by the concomitant use of intraocular pressure-lowering drugs (see Tables 1 and 2). Thus, all the methods of treatment can be further comprised of administering one of several intraocular pressure normalizing drugs in combination with, or in addition to, administering an IPREG-regulating composition (e.g., inhibits the expression or activity of up-regulated IPREGs and/or decreases the expression or activity of down-regulated IPREGs). The intraocular pressure normalizing drug can be administered at any time during treatment with the IPREG-regulating composition; thus, intraocular pressure normalizing drugs can be administered either continuously throughout the treatment with the compositions or before, after or concomitant with an effective amount of the compositions. As it is more likely that a human patient would already be undergoing therapy with an intraocular pressure lowering drug, the IPREG-regulating composition would likely be administered in addition to any intraocular pressure lowering drugs at intervals deemed appropriate by one of skill in the art to effectively treat the patient. There are a variety of drugs that can be used in the methods to lower intraocular pressure including: non-selective β1-adrenoceptor blockers, selective β1-adrenoceptor blockers, prostaglandins, prostaglandins analogs, carbonic anhydrase inhibitors, docosanoids, adrenergic agonists, cholinergic agents and miotics. In a particular embodiment, the intraocular pressure-lowering drug used the selective β1-adrenoceptor blocker betaxolol.

Dosage and Suitable Carriers

According to the methods of the invention, an effective amount of a composition that regulates (i.e., inhibits the expression or activity of and/or increases the expression or activity of) IPREGs can be administered to a mammal by an appropriate route (e.g., intraocular injection, topical conjunctival application, topical corneal application or using a mechanical delivery device) in an acceptable pharmaceutical carrier, either alone or in combination with another drug. An effective amount of the pharmaceutical composition is an amount sufficient to achieve the desired therapeutic or prophylactic effect, under the conditions of administration, for example, the amount of the composition administered such that RGC apoptosis, and, consequently, glaucoma progression is lessened and/or arrested. The composition can be administered in a single dose or in multiple doses to ensure that the patient sustains therapeutically significant levels of the compositions during treatment. The dosage can be determined by methods known in the art and will be dependent on the particular agent(s) chosen for the composition, the subject's age, body weight, sensitivity and tolerance to drugs and overall well-being.

Formulations of the compositions will vary according to the route of administration selected (e.g., solution or emulsion). Suitable pharmaceutical carriers can contain inert ingredients which do not interact with the regulatory substances in the compositions. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like.

Diagnostic Methods and Kits

Figures 5A, 5B:
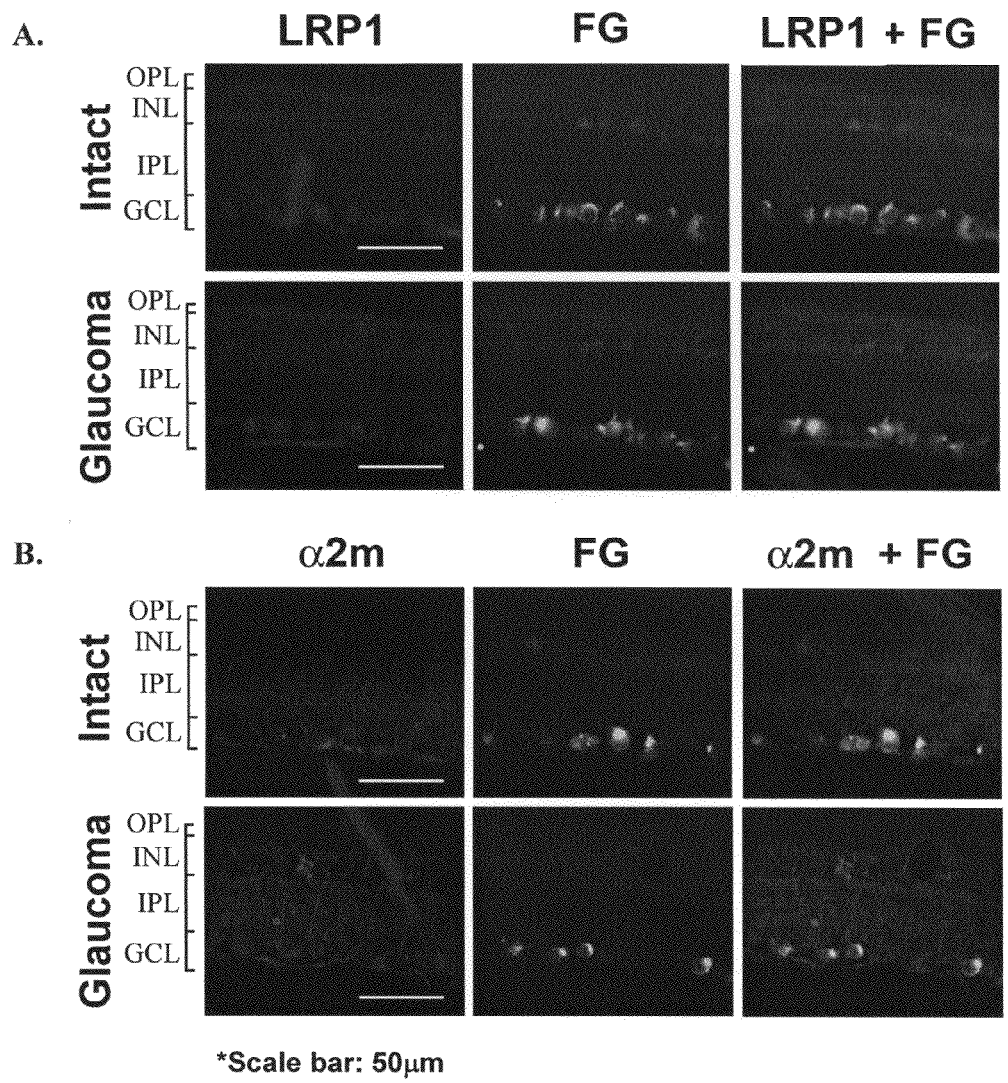
FIGS. 5A-5B are a series of confocal microscopy pictures illustrating the expression of α2 macroglobulin and LRP-1 receptors in normal and high IOP rat retinas as seen by immunohistochemistry. Expression of LRP-1 and up-regulation of α2 macroglobulin in glaucoma. Retinas were dissected from eyes (normal IOP or high IOP at day 28) and sections were prepared for immunohistochemistry with antibodies to α2 macroglobulin or LPR-1 receptors. Before dissection, RGCs were labeled retrogradely with fluorogold (FG) to ascertain RGC localization. Data were acquired by confocal microscopy.
Figures 5C, 5D:
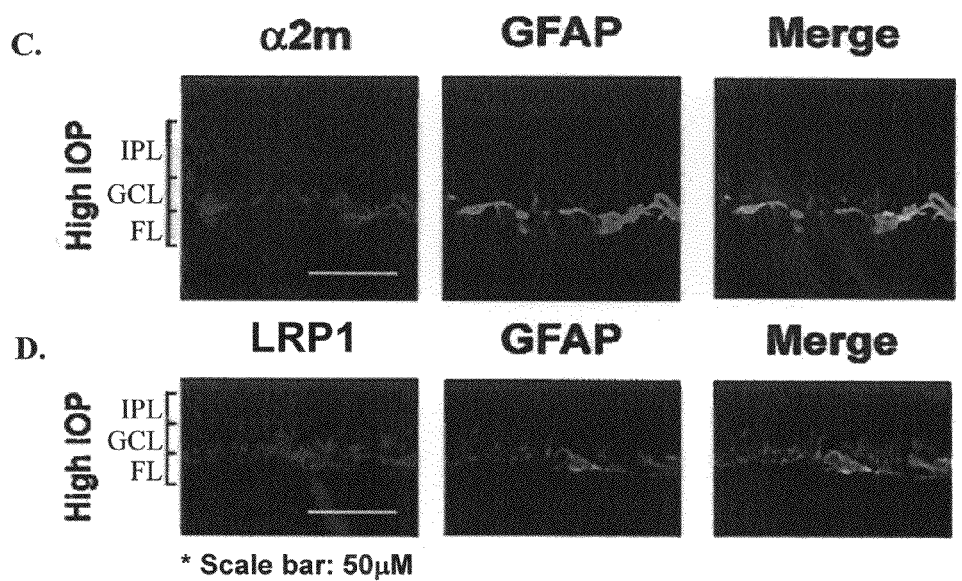
FIGS. 5C-5D are a series of confocal microscopy pictures illustrating the localization of α2 macroglobulin and LRP-1 receptors in normal and high IOP rat retinas as seen by immunohistochemistry. Retinas were dissected from rat eyes (normal IOP or high IOP at day 28) and sections were prepared for immunohistochemistry with antibodies to α2 macroglobulin or LRP-1 receptors and GFAP. Data were acquired by confocal microscopy.

The invention also relates to methods that allow the skilled clinician to diagnose glaucoma or glaucoma-related problems. The onset of high IOP is difficult to anticipate and, often, patients end up with exposure to high IOP for periods of time which are long enough that significant ocular degeneration has occurred, that is, before high levels of IOP are caught by and/or evident to a clinician. There are several identified IPREGs whose protein products showed a concomitant increase (up-regulated IPREGs) or decrease (down-regulated IPREGs) in expression levels (e.g., $\alpha 2$ macroglobulin, Amphiphysin 1 and G$z\alpha$). Further, many of the IPREG proteins are soluble and detectable in the aqueous humor of the eye (e.g., $\alpha 2$ macroglobulin). The aqueous humor liquid of the eye can be collected from the patient by standard surgical manipulation known to one of skill in the art. Soluble proteins can then be detected in the aqueous humor by any number of methods known in the art including immunoprecipitation, immunoblot, immunofluorescence, chromatography (e.g., HPLC, ion-exchange or gel filtration) or specific activity (e.g., cleavage of and/or binding to a detectably labeled substrate) and the expression levels of the detected proteins quantified. For example, FIG. 5 illustrates that in the aqueous humor of human eyes with glaucoma (G), $\alpha 2$ macroglobulin expression was detectable and significantly up-regulated.

Hence, the present invention relates to a method of testing for chronic ocular degeneration in a patient by measuring the expression level of one or more IPREG proteins in the aqueous humor of the patient and comparing the expression level of the one or more IPREG proteins measured to the expression level of the same one or more IPREG proteins in individuals with normal ocular function such that a higher expression level of IPREG proteins up-regulated in individuals with chronic ocular degeneration or a lower expression level of IPREG proteins down-regulated in individuals with chronic ocular degeneration in the patient indicates that the patient has chronic ocular degeneration. The expression level of the one or more IPREG proteins can be measured by any of the aforementioned methods as chosen by one of skill in the art, and can be compared to the expression level of the same one or more IPREG proteins measured using the same method as seen in an individual(s) with normal ocular function, for example, or in an individual(s) with ocular conditions that are characteristically (e.g., molecularly) different from glaucoma. The control and/or normal expression level of the one or more IPREG proteins can be measured in a sample from a normal individual at the same time as that measured in the patient or the expression level(s) used for comparison can be known, quantitated standards previously established for the particular method used.

The expression level of one or more, or even all of the IPREGs identified by the gene array analysis can be used measured in the method and, in a particular embodiment, the IPREG proteins whose expression level is measured are $\alpha 2$ macroglobulin and amphiphysin 1. Knowledge of the status of RGC stress in a patient is important to the skilled clinician in order to establish and/or illuminate glaucoma severity and progression. Thus, the present invention also relates to a method to test for the onset of RGC stress in a patient comprising measuring the expression level of one or more IPREG proteins in the aqueous humor of the patient at an initial time point; measuring the expression level of the same one or more IPREG proteins in the aqueous humor of the patient at a later time point; and comparing the expression level of the one or more IPREG proteins at the initial time point to that measured at the later time point such that a higher expression level of the one or more up-regulated IPREG proteins or a lower expression level of the one or more down-regulated IPREG proteins indicates the onset of RGC stress in the patient. Expression levels of one or more IPREG proteins can be measured and quantified in the patient's aqueous humor as discussed previously (e.g., using immunochemistry, chromatography or specific activity).

Further, it is well-known that individuals can respond differently to a particular therapy based on a number of environmental and genetic factors. Accordingly, the invention also relates to methods that, using changes to IPREGs that correlate with efficacy of treatment, predict the likelihood that a particular glaucoma therapy will be effective and, in particular, the likelihood that targeting one or more specific IPREGs in an individual for a glaucoma therapy will be useful and/or successful. Thus, in one aspect, the method relates to testing a biological sample (e.g., blood, cells or saliva) for genetic changes (e.g., gene duplication, deletion, recombination, transposition or sequence mutations) of an IPREG determined/known to be a marker of glaucoma therapeutic efficacy using any number of methods of nucleotide analysis (e.g., SNPs, fluorescent in situ hybridization (FISH), sequencing, PCR or mismatch detection assays) known to the skilled artisan. In another aspect, the method relates to measuring the expression level and/or activity in a biological sample (e.g., aqueous humor or cells) of an IPREG protein whose expression/activity has been identified as correlating with the success of a particular glaucoma treatment by the methods mentioned previously (e.g., immunochemistry, chromatography or substrate interaction) or by other methods known to those of skill in the art.

Kits for use in detecting the expression level of IPREG proteins in a biological sample (e.g., the aqueous humor) can also be prepared. Such kits can include antibodies or functional fragments which bind to one or more IPREG proteins, as well as ancillary reagents suitable for detecting the presence of a complex between the antibody (or antibody fragment) and the one or more IPREG proteins. The antibody composition can be provided in lyophilized form, either alone or in combination with additional antibodies specific for other epitopes of the one or more IPREG proteins being detected. The antibodies, which can be labeled or unlabeled, can be included in kits with adjunct ingredients (e.g., buffers, stabilizers, excipients, biocides and/or inert proteins, e.g. bovine serum albumin). For example, the antibodies can be provided as a lyophilized mixture with the adjunct ingredients, or the adjunct ingredients can be separately provided for combination by the user. Generally, these adjunct materials will be present in less than about 5% by weight based on the amount of active antibody, and usually will be present in a total amount of at least about 0.001% by weight based on antibody concentration. Where one or more second antibodies (e.g., secondary antibodies) capable of binding to the one or more antibodies reactive with the IPREG protein(s) (e.g., primary antibodies) are employed, such antibodies can be provided in the kit, for instance, in a second vial or container. The second antibodies, if present, are typically labeled, and can be formulated in an analogous manner with the antibody formulations described above. The components (e.g., anti-α$_2$ macroglobulin antibodies or antibody fragments and an ancillary reagent) of the kit can be packaged separately or together within suitable containment means (e.g., bottle, box, envelope or tube).

Pharmaceutical Compositions

The present invention also relates to pharmaceutical compositions for use in the methods of the invention to treat a mammal or patient. Thus, the invention relates to a pharmaceutical composition comprising an effective amount of at least one substance (e.g., molecule, compound, polypeptide) that inhibits the expression or activity of one or more up-regulated IPREGs and a pharmaceutically acceptable carrier, wherein the composition is administered to treat glaucoma. In a further embodiment, the pharmaceutical composition is also used to treat chronic ocular degeneration or RGC death. The pharmaceutical composition can be comprised of small interfering RNAs, antisense oligonucleotides, neutralizing antibodies, small molecules, recombinant gene expression vectors, recombinant gene viral vectors, synthetic peptides, recombinant polypeptides, peptidomimetics and inhibitors of the regulatory regions of the IPREGs. The up-regulated IPREGs inhibited by the pharmaceutical composition can be one of those of known or unknown function that were identified in the gene array analysis (see Table 2).

The present invention also relates to a pharmaceutical composition that comprises an effective amount of at least one substance that increases the expression or activity of one or more down-regulated IPREGs and a pharmaceutically acceptable carrier wherein the composition is administered to treat glaucoma. In one embodiment, the pharmaceutical composition is comprised of a substance (e.g., molecule, compound, polypeptide) that increases the expression or activity of those IPREGs found to be down-regulated in the gene array analysis (see Table 2) and this composition can be comprised of small interfering RNAs, antisense oligonucleotides, neutralizing antibodies, small molecules, recombinant gene expression vectors, recombinant gene viral vectors, recombinant polypeptides, peptidomimetics and activators of the regulatory regions of the IPREGs.

The invention further relates to a pharmaceutical composition comprising an effective amount of at least one substance that inhibits the expression or activity of one or more up-regulated IPREGs and at least one substance that increases the expression or activity of one or more down-regulated IPREGs and a pharmaceutically acceptable carrier, wherein the composition is administered to treat glaucoma and, in a further embodiment, chronic ocular degeneration or RGC death. The IPREGs targeted by the pharmaceutical composition can be any of those determined to have significantly altered expression in the gene array analysis using any substance that effectively and appropriately alters the IPREGs expression. As before, the pharmaceutical composition can be administered by one of several routes including intraocular injection, topical conjunctival application, topical corneal application or using a mechanical delivery device.

EXEMPLIFICATION

Example 1

Intraocular Pressure Regulated Genes

Induction of Intraocular Pressure
High IOP.
Episcleral cauterization of rat eyes was performed under anesthesia. After a conjunctival incision, extra-ocular muscles were isolated and the major limbal draining veins were identified based on location, relative immobility, larger caliber and branching pattern. Cauterization of three episcleral vessels in the right eye was done with a 30" cautery tip. The left eye in each animal was used as normal IOP control after sham-surgery (conjunctival incisions with no cauterization).

IOP Measurements.
IOP was gauged using a Tonopen XL tonometer under light anesthesia (intramuscular injection of ketamine, 4 mg kg; xylazine, 0.32 mg/kg; and acepromazine, 0.4 mg/kg). The accuracy of the readings of the Tonopen compared with other instruments, even under anesthesia, had already been determined. The average normal IOP of rats under anesthesia was 12 mm Hg (range 10-14 mm Hg), and in cauterized eyes it was elevated to a stable average 21 mm Hg (range 18-24 mm Hg) for longer than 4 months. These values were consistent with data previously published.

There were no IOP differences whether the left or the right eye were cauterized (data not shown); hence the right side was chosen for record and housekeeping purposes. Planar opthalmoscopy was used to confirm normal perfusion of the retina at elevated IOP. Cauterization caused an increase of ~1.7-fold in IOP. This increase was documented to be more relevant to human open angle glaucoma than other models that raise pressure>2-fold and often cause ischemia.

Pharmacological Reduction of High IOP.
A selective β-blocker (betaxolol 0.5%, Alcon) was applied daily as eye drops. Topical betaxolol was initiated as indicated (e.g. 3 days post-cauterization) resulting in full normalization of IOP after 3 days. Thereafter IOP continued to remain normalized while betaxolol was applied. For example, when betaxolol was applied from day 3 post-cauterization onwards, those eyes suffered high IOP from day 1-6, and had normalized IOP from day 7 onwards. Betaxolol had no significant effect in the IOP of normal eyes.

High IOP was induced in rat eyes by cauterizing three episcleral vessels of one eye to reduce aqueous humor outflow, and the contralateral eyes were sham-operated and were used as controls (FIG. 1A). The IOP of cauterized eyes was significantly higher than control eyes at 3, 7, 14, 21 and 28 days after vein cauterization (p#0.01). The mean IOP in glaucomatous eyes was approximately 21 mm Hg compared with a mean IOP of approximately 12.6 mm Hg in normal eyes. Daily topical treatment with betaxolol lowered aqueous humor production and reduced high IOP induced by cauterization, but had no significant effect on normal IOP in contralateral eyes (see FIG. 1A). Betaxolol application starting at day 3 post-cauterization fully normalized high IOP from day 7 onward. There were no significant differences in the IOP of cauterized eyes treated with betaxolol, versus control eyes with or without betaxolol (FIG. 1A).

RGC Death Induced by High IOP
Chronic high IOP caused by vein cauterization causes cumulative RGC loss at a constant rate (Rudinski M et al., *J Neurobiol* 58:341-354, 2004). Using retrograde tracers that label RGC bodies within the retina, we confirmed that at 3, 4 and 5 weeks post cauterization there was an average RGC loss of approximately 15%, 20% and 27%. At 6 weeks post-cauterization there was an average RGC loss of approximately 35% (not shown). Normalization of IOP with betaxolol reduced the average rate of RGC loss, but did not prevent it (FIG. 1B). In the experiment shown, administration of daily betaxolol normalized IOP from day 7 onwards. Thus, a lesser but still significant rate of RGC loss was triggered by short-term (approximately 1 week) exposure to high IOP but this death was independent of continuous high IOP. These animal data replicated the reported visual field loss in patients medicated to lower IOP, which affected 25% of subjects at 3 years and greater than 70% at 10 years (Kass M A et al., *Arch Opthalmol* 107:1590-1598, 1989; O'Brien C et al., *Am J Opthalmol* 111:491-500, 1991).

RGC Death Induced by Optic Nerve Axotomy

To contrast with glaucoma (which is chronic intraocular damage), optic nerve axotomy, which is an acute extraocular damage, was studied. In optic nerve axotomy, minimal but detectable RGC death was seen after 4 days and approximately 40% RGC was found 10 days post-injury (Berkelaar M et al., *J Neurosci* 14:4368-4374, 1994; Di Polo A et al., *Proc Natl Acad Sci* 95:3978-3983, 1998). Because the glaucoma and axotomy in vivo models afforded comparable RGC loss, in further experiments, day 28 after induction of high IOP was compared to day 4 after optic nerve axotomy, and day 42 after induction of high IOP was compared to day 10 after optic nerve axotomy.

Intraocular Pressure Regulated Early Genes (IPREGs)

RNA preparation. Total RNA was isolated from retinal tissue using TRIZOL® (Life Technologies). Three retinas belonging to the same experimental group were pooled for the gene microarray experiment. RNA was then further purified using the RNAEASY® (QIAGEN®). The integrity of the RNA samples was assessed by running aliquots on RNA 6000 Nano LabChip (Agilent) using the 2100 bioanalyzer (Agilent).

Microchip Hybridization.

Probe synthesis, hybridization and scanning were done according to Affymetrix protocol, as a service at the McGill University and Genome Quebec Innovation Centre. For the experiments shown, Rat U34 Genome Arrays (8,700 genes, Affymetrix) were used. Briefly, RNA samples were first converted to double stranded cDNA (T7-(dT)24 primer (Genset)). Then the cDNAs were purified and used to generate the biotinylated cRNA probes (Bioarray High Yield RNA transcript labeling kit (Enzo diagnostics)). An aliquot of the purified cRNA was analyzed on RNA 6000 Nano LabChip (Agilent) to verify the integrity and size distribution. Immediately after hybridization the chip was placed in the Affymetrix GeneChip Fluidics Station 400 (Affymetrix). In total, 10 low-stringency washes (63 SSPE, 0.01% Tween-20, 0.005% Antifoam) and 4 high-stringency washes (100 mM MES, 0.1 M NaCl, 0.01% Tween-20, 50 C) were performed (all reagents from Sigma). The array was then incubated with SAPE® (streptavidin/phycoerythrin stain, Molecular Probes), followed by 10 low stringency washes. The array was incubated with biotinylated anti-streptavidin antibody (Vector Laboratories) and washed again with 15 low stringency washes. Specifically bound probe was detected by placing the array in the Agilent GeneArray scanner 2500 (Affymetrix). The scanned images were analyzed using the Microarray Analysis Suite version 5.0 (Affymetrix). Statistical analyses were done with the help of the Kensington Discovery Edition version 1.8 (Inforsense).

Figure 2:
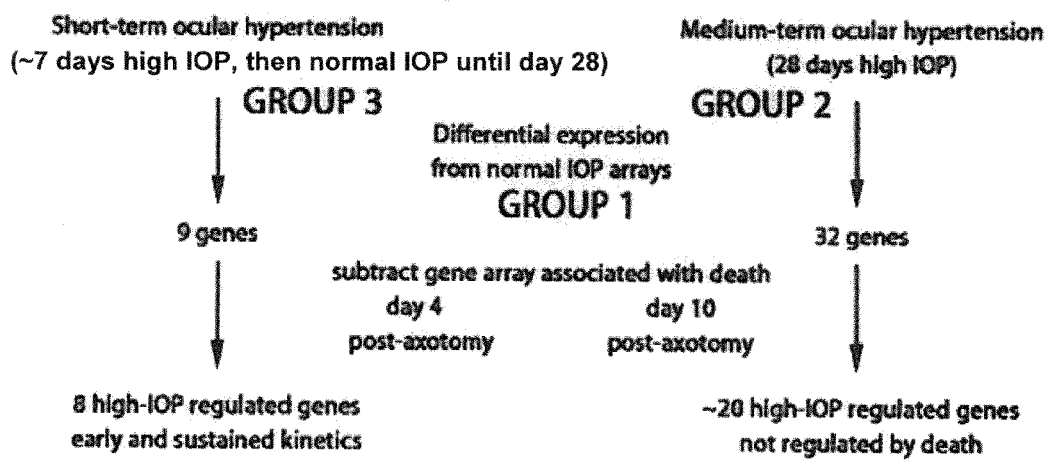
FIG. 2 is a flowchart illustrating the experimental procedure for recovery of retinal mRNA samples for differential gene arrays. Retinas were microdissected from the indicated eyes, mRNA were prepared freshly and studied by differential gene arrays (see data in Table 1.)

Retinas were carefully dissected out to insure that only retinal mRNAs were prepared for gene microarray studies. Samples were obtained from sham operated eyes (normal IOP control, Group 1), eyes at 28 days high IOP (test, Group 2), and eyes 28 days after cauterization plus daily betaxolol treatment from day 3 onwards (Group 3). In Group 3, high IOP returned to normal levels by day 7. Samples from each of these groups (n=4 each group) were studied by gene microarrays (see FIG. 2 flowchart). A cutoff of 2.5-fold was used to afford significance (p<0.05).

Initial analyses focused on differential expression in retinas subjected to high IOP (Group 2) versus normal IOP (Group 1). The expression of thirty-two genes was significantly altered in Group 2, some were decreased and others were increased at day 28 of high IOP. These genes were putative Intraocular Pressure Regulated Early Genes (IPREGs) (Table 1).

TABLE 1

Results of gene arrays. cDNA-array data comparing day 28 high IOP (column A) versus normal IOP (column B) eyes cauterized for 28 days but subject to only 7 days of high IOP (betaxolol from days 4-28) versus normal IOP. In both cases, the change relative to non-cauterized eyes are shown.

| | | | Relative Change versus non-cauterized eyes | |
|---|---|---|---|---|
| Name | Genebank number | Proposed Function | cauterized high IOP A | cauterized + betaxolol B |
| Signaling Pathways | | | | |
| 1 α2 macroglobulin | M23566 | Multifunctional | 16.3 | 5.6 |
| 2 cDNA clone rx00382 | AI639155 | Methyl-transferase | 7.6 | 7.2 |
| 3 PSD-95/SAP90-asociated protein-4 | U67140 | Receptor Adaptor | 5.8 | −1.0 |
| 4 Reggie1-1 | AF023302 | RGC regeneration | 3.9 | 1.8 |
| 5 RBCK | AB011369 | PKC1-associated | 3.2 | 1.3 |
| 6 Gzα | U77483 | Signal transduction | 2.8 | 1.1 |
| 7 Protein phosphatase 1 gamma | S78217 | Signal transduction | 2.6 | 2.5 |
| 8 Amyloid precursor-like protein 2 | X77934 | Multifunctional | −2.6 | 1.1 |
| 9 Amphiphysin 1 | Y13381 | Endocytosis | −2.8 | −1.1 |
| 10 Crybb2 | X83671 | Transcription factor | −3.3 | −1.0 |
| 11 Ras-related p23 | X12535 | Survival/apoptosis | −4.0 | 1.1 |
| Structural Proteins | | | | |
| 12 cDNA clone rx01295 | AI639375 | WD rich protein | 6.9 | 4.8 |
| 13 Ribosomal protein L23-related product | U62635 | Ribosomal protein | 6.5 | 3.8 |

TABLE 1-continued

Results of gene arrays. cDNA-array data comparing day 28 high IOP (column A) versus normal IOP (column B) eyes cauterized for 28 days but subject to only 7 days of high IOP (betaxolol from days 4-28) versus normal IOP. In both cases, the change relative to non-cauterized eyes are shown.

| | Name | Genebank number | Proposed Function | Relative Change versus non-cauterized eyes | |
|---|---|---|---|---|---|
| | | | | cauterized high IOP A | cauterized + betaxolol B |
| 14 | Clone RKIAS43 | AA892520 | Vesicle protein | 5.1 | 2.9 |
| 15 | Gial fibrillary acidic protein | AF028784 | Glial marker | 4.0 | 1.4 |
| 16 | Cyclic nucleotide-gated cation channel | AJ000515 | Sensory channel | 4.0 | 3.4 |
| 17 | SPARC | U75928 | | 2.6 | 1.9 |
| 18 | Helicase RAP 30 | L01267 | DNA repair | −2.8 | 1.2 |
| 19 | Proteasome rPA28 subunit beta | AA892801 | Protein degradation | −2.9 | |
| 20 | ATPase alpha-1 subunit | M74494 | ATPase | −3.3 | 1.5 |
| 21 | Beta A3/A1 crystallin | X15143 | chaperone | −3.6 | −1.1 |
| 22 | Beta A4 crystallin | AF013247 | chaperone | −5.7 | |
| | | Metabolic pathways | | | |
| 23 | B-2 arylamine N-acetyltransferase | U01347 | Melatonin synthesis | 4.4 | 1.5 |
| 24 | cDNA clone rx05013 | AI639441 | Initiation factor | 3.8 | 2.8 |
| 25 | S-adenosylmethionine synthase | J05571 | Methyl donor | −2.7 | 1.1 |
| 26 | Asparagine synthase | U07201 | Asn synthesis | −2.8 | −1.1 |
| | | ESTs | | | |
| 27 | Clone rx05013 | AI639441 | | 3.8 | |
| 28 | Clone rx03980 | AI639207 | | 2.6 | |
| 29 | EST189275 | AA799778 | | 2.5 | |
| 30 | Clone rx01612 | AI639465 | | −2.6 | |
| 31 | EST213677 | AI104388 | | −2.6 | |
| 32 | EST196604 | AA892801 | | −3.0 | |
| 33 | Clone rx01394 | AI639406 | | −5.1 | |

A further comparison was performed for normal IOP (Group 1) versus cauterized eyes with high IOP for 7 days and normal IOP for another 21 days (Group 3), and demonstrated completely normal expression for most candidate IPREGs. Their expression was not different from normal IOP retinas. Normalization of expression of these genes could occur because i) RGC stress/death was prevented, ii) altered expression required sustained ocular hypertension for 28 days, or iii) altered expression is short-lived.

Importantly, however, eight candidate IPREGs retained significantly altered expression versus normal IOP retinas despite complete normalization of IOP (Table 2). Amphiphysin, AMPLP-2, Beta A4 crystallin and ras-related p23 expression was down-regulated and α2 macroglobulin, Gzα, PTP-1γ, reggie1-1 and PSD95/SAP90-associated protein 4 expression was up-regulated. Normalization of IOP from day 7 to day 28 did not reverse the changes in expression of three genes (clone rX00382, protein phosphatase-1 gamma and cyclic nucleotide-gated cation channel); only partially reversed the changes in expression of five genes (α2 macroglobulin, Reggie 1.1, clones rX01295 and rX05013, ribosomal protein L23 related product and vesicular protein clone RKIAS43); but it fully reversed up-regulation of Gzα (Table 2).

TABLE 2

| | | Confirmed by | |
|---|---|---|---|
| Name | Proposed Function | Quantitative Normal IOP | RT-PCR day 28 IOP |
| Complete criteria | | | |
| α2 macroglobulin | Multifunctional | |  |
| cDNA clone rx00382 | Methyl-transferase protein | | 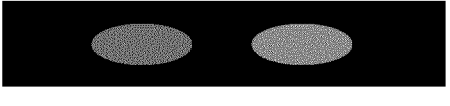 |
| Reggie1-1 | RGC regeneration | | |
| Protein phosphatase 1 gamma * | Signal transduction | | |
| cDNA clone rx01295 * | WD rich protein | | |
| Ribosomal protein L23-related product | Ribosomal protein | | |
| Clone RKIAS43 | Vesicle protein | | |
| Cyclic nucleotide-gated cation channel | Sensory channel | | |
| CDNA clone rx05013 | Initiation factor | | |

TABLE 2-continued

| Name | Proposed Function | Confirmed by Quantitative Normal IOP | RT-PCR day 28 IOP |
|---|---|---|---|
| Partial criteria | | | |
| PSD-95/SAP90-asociated protein-4* | Adaptor for receptor activity | [blot] | [blot] |
| Gzα | Signal transduction | [blot] | [blot] |
| Amyloid precursor-like protein 2* Amphiphysin 1 * | Multifunctional Endocytosis | [blot] | [blot] |
| Helicase RAP 30 | DNA repair | | |

Selected genes that meet the criteria of IPREGs.
From Table 1a subset of genes that met all the criteria for IPREGs is listed.
Other genes that partially meet the criteria are selected also.
*indicates neuron specific proteins, while the other proteins are expressed in other cell types.
Data shown for semi-quantitative RT-PCR is representative of 3 independent studies.
Equal amounts of mRNA and equal gel loading were ascertained (data not shown).

It is important to note that the genes whose expression was completely normalized 21 days after betaxolol treatment (e.g., Gzα) could still be interesting candidates. Also, it is possible that these genes could be long-lived, although for shorter times than the 21 days post-normalization of IOP that we studied in our experimental paradigm (see Table 3 for examples).

TABLE 3

Therapy in glaucoma targeting α2 macroglobulin with neutralizing antibodies. Each data point represents the average of at least 6 eyes (±sd). RGC labeling was done by retrograde of a dye from the SC. A "—" indicates "no treatment". Ocular pressure was not affected by intraocular injections.

| | | Treatment | | | RGC loss (%) |
|---|---|---|---|---|---|
| Row | IOP at day 1 | Daily Betaxolol (days 14-42) | Days 14 and 21 Ab injection | IOP history | at day 42 vs normal) |
| 1 | Normal | — | — | Normal | 0 ± 0 |
| 2 | Normal | — | control serum | Normal | 5 ± 4 |
| 3 | High | — | — | High 42 days | 33 ± 6 |
| 4 | High | — | — | High 28 days | 19 ± 5 |
| 5 | High | — | — | High 14 days | 8 ± 5 |
| 6 | High | — | control serum | High 42 days | 30 ± 6 |
| 7 | High | — | anti-α2 serum | High 42 days | 21 ± 3 |
| 8 | High | d-14 to 42 | — | 14 days high, 28 normal | 19 ± 1 |
| 9 | High | d-14 to 42 | control serum | 14 days high, 28 normal | 21 ± 5 |
| 10 | High | d-14 to 42 | anti-α2 serum | 14 days high, 28 normal | 11 ± 4 |

These data indicated that changes in retinal expression of the eight genes required 7 days or less of retinal exposure to high IOP. Furthermore, changes in expression were sustained for a subsequent period of 21 days in the absence of ocular hypertension, indicating that the changes are long lived. Changes in retinal gene expression seemed to precede RGC loss, because RGC death was minimal in this paradigm. Thus, these findings strongly suggested that these genes may be implicated in RGC death, especially in RGC death that continues after normalization of IOP.

Confirmation of Gene Microarrays

Kinetics analyses. All studies (Gene arrays, RT-PCR, Northern blots, Westerns blots, counting of retrograde labeled RGCs) were done on freshly isolated retinas from control (sham-operated) or cauterized eyes at the indicated days after surgery.

RT-PCR. Retinas from control, high IOP, or axotomized animals were dissected on the indicated days. Total retinal RNA was extracted (Trizol, GIBCO), DNA was digested (Dnase, amplification grade, GIBCO), and samples were re-purified after a second Trizol extraction. For RT-PCR analysis single retinas were used (n=3-5). One μg of total retinal RNA and specific primers (SIGMA) were used to generate the complementary cDNA. PCR amplification of cDNAs was carried out with specific primers for each gene. For PCR stringent conditions were followed pertaining to semi-quantitative PCR analysis. Linear amplification of candidate genes was obtained after a total of 30 cycles, while β-actin (used as internal control) was in the linear range after 18 cycles. Agarose gels resolving the PCR products were scanned using a STORM 840 imaging system and quantitative analyses were performed using imagequant analysis software, in three independent RT-PCR experiments using three independently prepared RNA samples. Readings were averaged±SEM and data for each gene product in each group (normal IOP and high IOP) were standardized against β-actin as an internal control (100%). Retinal β-actin mRNA expression levels did not vary upon increase in high IOP (data not shown).

Figure 3:
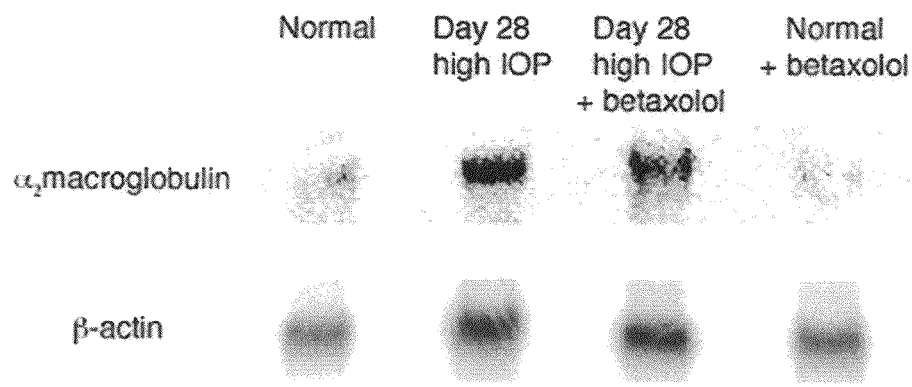
FIG. 3 is a Northern blot illustrating the upregulation of the α2 macroglobulin transcript in glaucoma rat retinas. Retinas were dissected from eyes treated as indicated (n=3) and mRNAs were purified and studied by Northern blotting with labeled α2 macroclobulin or actin (control) probes. Data representative of two independent experiments.

To confirm the results from the gene microarray analysis, quantitative RT-PCR was performed with primer pairs specific for some candidate IPREGs. Several RT-PCR experiments with independently isolated retinal mRNA samples confirmed quantitatively the down-regulation of amphiphysin, AMPLP-2, Beta A4 crystallin, and ras-related p23; and the up-regulation of α2 macroglobulin, Gzα, PTP-1α, reggie1-1, and PSD95/SAP90-associated protein 4 (see Table 3, some data not shown).

α2 macroglobulin was selected for further study. Northern blot analysis for retinal α2 macroglobulin mRNA showed an approximately 3 fold increase at day 28 of high IOP compared to normal IOP (p<0.001). This increase was attenuated slightly by betaxolol treatment, but was still significantly increased over normal IOP. In contrast, control retinas of normal IOP with or without betaxolol treatment had normal and comparable α2 macroglobulin mRNA (FIG. 3).

Specific Regulation of IPREGs by Ocular Hypertension

Optic nerve axotomy. Female Wistar rats between 250-300 grams were anesthetized with a cocktail of xylazine, acepromazine and ketamine. Access to the eye bulb was obtained by opening the dorsal orbita, and partially removing the tear glands and orbital fat. Visualization of the optic nerve (ON) was obtained by separation of the superior rectus muscle followed by the incision of the eye retractor muscle. A longitudinal incision of the meninges was made 5 mm behind the bulbar exit of the ON, avoiding blood vessels so that retinal circulation would not be compromised. Sectioning of the ON was made 5 mm posterior of its exit from the eyeball so that the optic nerve head would not be compromised. All animal procedures were approved by the McGill Animal Welfare Committee.

Western Blotting.

Single retinas were homogenized and lysed (150 mM NaCl, 50 mM Tris pH 8.0, 2% NP-40, PMSF, leupeptin and aprotinin) for 45 min. After centrifugation to remove nuclei and debris, soluble protein concentrations were determined using a kit (BIORAD). Fifteen g of retinal proteins/lane were fractionated on a 12% SDS-PAGE, and transferred to a nitrocellulose membrane. The α2 macroglobulin protein was detected using a goat polyclonal antibody against rat α2 macroglobulin (Sigma and Calbiochem). Pure rat α2 macroglobulin protein (Sigma) was used as control. Horseradish peroxidase (HRP)-conjugated antibodies were used as secondary reagents. Immunoreactive bands were revealed with enhanced chemoluminescence (NEN).

To determine whether ocular hypertension, and not RGC death, was the specific regulator of gene expression the glaucoma model was compared to the optic nerve axotomy model. Quantitative western blotting of retinal protein was performed with samples from normal IOP, day 28 high IOP and day 4 ON axotomy. These time points for each model were chosen to study molecular changes that precede significant RGC death.

Figure 4:
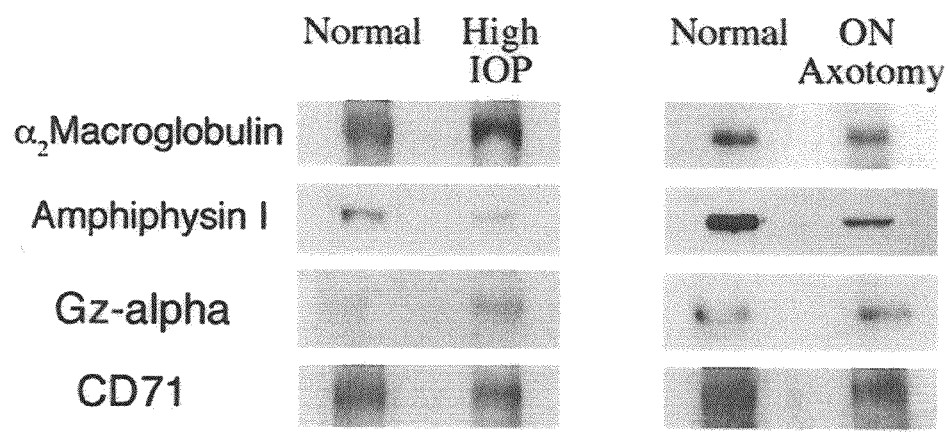
FIG. 4 is an immunoblot illustrating the protein expression levels of α2 macroglobulin, amphiphysin 1 and Gzα in normal, glaucoma and optic nerve axotomy rat retinas. Quantification of protein expression in normal versus glaucoma versus axotomy. Retinas were dissected from eyes treated as indicated (n=3), and whole protein detergent extracts were studied by western blottin with specific antibodies. CD71 was used as an internal control (100%) as its expression does not change in any condition. Data representative of 3 independent experiments.

Retinal α2 macroglobulin protein expression was significantly up-regulated 2.3-fold in high IOP, but were not altered in optic nerve axotomy (FIG. 4). In contrast, in the glaucoma and the optic nerve axotomy models there were comparable changes for retinal levels of Gzα protein (increased 64% and 43% respectively) and amphiphysin (decreased ~30% in both models). Thus, Gzα and amphiphysin changes were not specifically regulated by high IOP; instead they may be markers of RGC damage, while α2 macroglobulin was specifically induced by ocular hypertension.

Example 2

Validation of a Role for α2 Macroglobulin in Glaucoma

Localization of α2 Macroglobulin and its Receptor in Retina Retrograde RGC Labeling.

RGCs were labeled with 3% DII (1,1-dioctadecyl-3,3,3,3-tetramethylindocarbocyanine perchlorate) or with 3% fluorogold. Briefly, Wistar rats were anesthetized and their heads were mounted in a stereotactic apparatus. Both superior colliculi (SC) were exposed and the dye was injected in two adjacent sites at the SC of each hemisphere (5.8 mm behind Bregma, 1.0 mm lateral, and depth 4.5 mm for the first release of dye solution and 3.5 mm for the second release).

Flat Mounted Retinas and RGC Counting.

7 days after dye injection, the vasculature of the rats were perfused-fixed (transcardiac perfusion in phosphate-buffer (PB), followed by 4% PFA in PB) and the eyes were enucleated. After post-fixing for 1 hour cuts were made through the sclera to form a Maltese cross pattern and retinas detached from the eyecup at the optic nerve head. The retinas were flat-mounted on glass slides (vitreous side up) air-dried and cover-slipped with mounting medium (Molecular Probes). The retinas were observed under fluorescence microscopy (Zeiss). For each retina, four digital images from each quadrant (superior, inferior, nasal and temporal) were taken at 20×. RGCs were recognized in flat mounted retinas by the presence of retrogradely transported dye and by morphology. RGCs in all 4 quadrants (16 images per retina) were averaged and presented as RGCs/mm of area counted.

Immunohistochemistry and Confocal Microscopy.

Rats were perfused intracardially as above and their eyes enucleated, removing the anterior part and the lens. The remaining eyecups were immersed in 4% PFA for 2 hours, then transferred to 30% sucrose for several hours at 4° C., embedded in OCT (tissue-Tek, Miles Laboratories, IN) and frozen in methyl butane in liquid nitrogen. Radial cryosections (10-14 m) were placed onto gelatin-coated slides. Sections were blocked using 3% BSA in PBS with 1% Triton for 30 min at room temperature and exposed to the primary antibody for 2 h: anti-α2macroglobulin antibody (rabbit, 1:200 (Calbiochem) or Goat, 1:100 (Sigma)) and/or anti-LRP1 receptor (1:200 Santa Cruz). Double staining was carried out with antibodies directed to the glial marker glial fibrillary acidic protein (GFAP) (mouse, 1:400 Chemicon) or to the neuronal marker Tubulin III (mouse, 1:2000, Chemicon). Secondary antibodies were FITC-conjugated anti-mouse, Cy3-conjugated anti-rabbit, or Alexa Fluor 488 anti-goat (used at 1:250, 1:1000 or 1:500 dilutions) incubated for 1 h at room temperature. Confocal images were recorded on a Zeiss confocal microscope (LSM510).

Because α2 macroglobulin is a soluble protein, its localization and also that of its cellular receptor (LRP-1) were studied (see FIGS. 5A-5D). In normal retinas α2 macroglobulin was found in the vast majority of RGCs, where it co-localized with retrograde tracer Fluorogold label and Tubulin βIII an RGC-specific marker (data not shown), but it also localized in Müller cells and retinal astrocytes. Positive immunostaining for LRP-1 receptors also co-localized with Fluorogold-positive neurons. In normal retinas, LRP-1 immunostaining was detected almost exclusively in RGCs, whereas in glaucoma (day 28 cauterized with high IOP) LRP-1 expression remained high in RGCs, but it was also detected in the fiver layer where it co-localized with GFAP in presumptive astrocytic and Müller cell processes. Similar data of α2 macroglobulin up-regulation and LRP co-localization were obtained in studies using retinal sections prepared from rats with hypertension induced by the hypertonic saline model of glaucoma (data not shown), suggesting that the results were not specific to one animal model of glaucoma.

Figure 6:
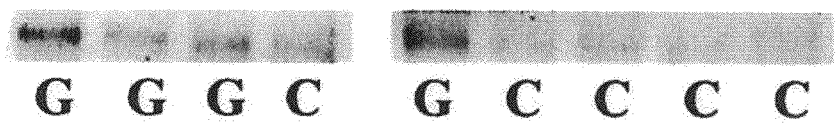
FIG. 6 is an immunoblot illustrating the expression of α2 macroglobulin in the aqueous humor of human eyes with glaucoma (G) and cataract (C). Aqueous humor samples were taken during surgery from patients with glaucoma (G) or cataracts (C). Equal amounts of protein were loaded in every lane (10 mg), and blots were probed with anti-a2 macroglobulin antibody. n=8 for glaucoma and n=7 for cataracts.

Semi-quantitative western blot analyses from rat aqueous humor, demonstrated a significant increase of activated α2 macroglobulin protein in eyes with high IOP compared with normal contralateral eyes (data not shown). Consistent with these findings, semi-quantitative studies using human aqueous humor collected during surgeries demonstrated that activated α2 macroglobulin protein was on average significantly increased in aqueous humor of glaucoma, but not cataract patients (FIG. 6).

Together, the data indicated that α2 macroglobulin is up-regulated in ocular hypertension in 2 rat animal models and in humans, that α2 macroglobulin is co-localized with its receptor LRP-1 in RGCs and in other retinal layers, and also is present in aqueous humor.

Validation In Vivo of α2 Macroglobulin as a Therapeutic Target for Glaucoma

Intraocular Injections.

A conjunctival incision was performed in the superior temporal quadrant of the eye. A puncture was made on the eye wall with a 30 G needle to allow the entrance of a cannula in the orbit. A glass cannula (10 µm thickness), prepared with an upright microelectrode puller (Narishige) was connected through plastic tubing to a Hamilton syringe to dispense solutions of anti-α2 macroglobulin rabbit antibody (Calbiochem), control PBS, or control rabbit antibody (Sigma). Injections were done at day 14 and 21 post-surgery (in sham-operated control eyes with normal IOP, and cauterized eyes with high IOP). The intraocular injections were in 2 µl volumes containing a total of 2 µg antibody. This amount was selected because in quantitative western blots of whole rat retina there was an estimated total of ~1 µg of α2 macroglobulin in glaucomatous eyes (data not shown). Ocular pressure was not affected by intraocular injections, the high IOP eyes remained high IOP and the normal IOP eyes remained normal IOP (data not shown).

The interaction of α2 macroglobulin with LRP-1 has been shown to be deleterious to neurons (Lopes MB et al., *FEBS Lett* 338:301-305, 1994; Yepes M et al., *J Clin Invest* 112: 1533-1540, 2003) including RGCs (Birkenmeier G et al., *Neuroreport* 8:149-151, 1996; Birkenmeier G et al., *FEBS Lett* 416:193-196, 1997; Herz J, *J Clin Invest* 112:1483-1485, 2003).

To evaluate the potential role of α2 macroglobulin in the death of RGCs, α2 macrobglobulin protein was microinjected in normal eyes to determine whether glaucoma-like RGC death ensued. In this paradigm, a total of 1-2 µg of α2 macroglobulin were delivered by a single intraocular injection in normal eyes, and surviving RGCs were counted at days 14 or 28 post-injection, by retrograde labeling. The 1-2 µg quantity was selected to best mimic the total amount of α2 macroglobulin quantified from the aqueous humor glaucomatous eyes in the rat model of ocular hypertension (data not shown).

Acute intraocular injection of α2 macroglobulin resulted in the progressive loss of RGCs compared to a group of contralateral eyes injected with a PBS vehicle. In three, independent experiments (n=3, 2 and 6 eyes per group), there were RGC losses of 11±3% (p≤0.01) and 28±11% (p≤0.001) respectively 2 weeks and 4 weeks after injection of α2 macroglobulin compared to vehicle PBS.

These data suggested that α2 macroglobulin induces progressive RGC death with kinetics comparable to that induced by ocular hypertension. Together with the previous results showing continuing over-expression of α2 macroglobulin mRNA and protein independent of high IOP, these results helped explain progressive RGC death after normalization of high IOP.

A second paradigm was used to confirm the role of α2 macroglobulin in RGC death. Neutralizing antibodies to α2 macroglobulin were injected intraocularly in glaucomatous eyes with high IOP to determine whether RGC death could be prevented. The experimental model was to induce high IOP for 14 days to trigger α2 macroglobulin over-expression and RGC damage, before the initiation of α2 macroglobulin neutralizing therapy. Neutralization was used as single therapy, or was combined with daily betaxolol treatment to better reflect the clinical setting in which glaucoma patients would be simultaneously treated with pressure-lowering drugs. Neutralizing antibodies were given at days 14 and 21 after cauterization, and surviving RGCs, identified by retrograde labeling, were counted at day 42 post-surgery. In this protocol, there were no antibodies given between days 21 and 42. Control rats were treated with either control antibodies, saline, or were not injected (see Table 3).

After 42 days of high IOP, there was a loss of 33±6% RGCs compared to normal IOP (Table 3 row 3 versus row 1). RGC loss in high IOP was time-dependent. There was a loss of 19±5% RGCs at day 28 high IOP, and 8±5% RGCs at day 14 high IOP (Table 3, rows 4 and 5). Normalization of IOP with daily application of betaxolol (from day 14 to 42) significantly reduced the loss of RGCs to 19±1% (Table 3 row 8 versus row 3). Two single intraocular injections of anti-α2 macroglobulin antibody at days 14 and 21 of glaucoma reduced RGC loss to 21±3% (Table 3, row 7 versus rows 6 and 3). Treatment with anti-α2 macroglobulin antibody in combination with betaxolol was markedly neuroprotective, significantly reducing RGC loss to 11±4% (Table 3 row 10 versus row 9). This combined treatment was significantly better than either treatment alone (Table 3, row 10 versus 7 and 8). RGC counts in the combination treatment were not statistically different from RGC counts in normal IOP eyes injected intraocularly with control antibodies (Table 3, row 10 versus row 2), and were not statistically different to eyes subjected to 14 days of high IOP (Table 3, row 10 versus row 5).

Control intraocular injections of control antibody or saline did not alter RGC counts in normal retinas (data not shown) or at day 42 of glaucoma (Table 3, row 6 versus row 3), and did not alter the protective effect of IOP normalization with betaxolol (Table 3, row 8, versus row 9).

Discussion

α2 Macroglobulin Gene Up-Regulation

The α2 macroglobulin gene and protein were up-regulated after only approximately 7 days of high IOP, with sustained expression that persisted for more than 20 days independently for ocular hypertension. Induction of α2 macroglobulin mRNA was specific to high IOP, and it did not increase following optic nerve axotomy. Hence, short-term ocular hypertension was sufficient to cause high pressure-specific, long-lasting increases in the retina. These data identified α2 macroglobulin as an IPREG in the cautery rat model of glaucoma, as well as in the hypertonic saline rat model of glaucoma (data not shown), and higher expression was also demonstrated in human eyes with glaucoma compared to eyes with cataracts.

Mechanisms of α2 Macroglobulin Damage

The α2 macroglobulin protein and its LRP-1 receptor are present abundantly in RGCs in glaucoma, and LRP-1-α2 macroglobulin interactions are deleterious to various types of neurons (Lopes MB et al., *FEBS Lett* 338:301-305, 1994; Yepes M et al., *J Clin Invest* 112:1533-1540, 2003), including RGCs (Birkenmeier G et al., *Neuroreport* 8:149-151, 1996; Birkenmeier G et al., *FEBS Lett* 416:193-196, 1997; Herz J, *J Clin Invest* 112:1483-1485, 2003).

Consistent with the neurotoxic role of α2 macroglobulin, intraocular delivery of this protein in normal eyes caused glaucomatous-like RGC loss; whereas neutralization of this protein significantly reduced or delayed RGC death in glaucoma especially when combined with pressure-normalizing drugs.

Neurotoxic mechanisms include increasing $iCa^{++}$ through activation of NMDA receptors (NMDAR), and modulation of glutamate neurotransmission in hippocampal neurons (Bacskai B J et al., *Proc Natl Acad Sci* 97:11551-11556, 2000; Qui Z et al., *J Biol Chem* 277:14458-14466, 2002; Qui Z et al., *Neuroscience* 122:291-303, 2003; Qui Z et al., *J Biol Chem* 279:34948-34956, 2004). Thus, up-regulation of α2 macroglobulin in the eye can potentiate the normal excitatory activity of NMDAR leading to RGC death. Also, α2 macroglobulin binds to and neutralizes retinal neurotrophins, in particular Nerve Growth Factor (NGF) (Chiabrando G A et al., *J Neurosci Res* 70:57-64, 2002; Skomicka E L et al., *J Neurosci Res* 67:346-353, 2002), which is an important survival or maintenance factor for RGCs. Thus, α2 macroglobulin over-expression would lead to decreased growth factor bioavailability (see model in FIG. 7) and may be one explanation of why delivery of exogenous NGF does not protect RGCs in glaucoma.

Relationship of Other Up-Regulated Genes and RGC Damage

Other IPREGs seen to be up-regulated in ocular hypertension can be linked to RGC death. It is particularly interesting that some of these IPREGs can work in cooperation with α2 macroglobulin.

Up-regulated PSD95/SAP90-associated protein-4 (PSD95/SAP90) and the GTPase Gzα are associated with NMDAR activity. PSD95/SAP90 and bind NMDAR C-termini at sites distinct from spectrin (Wechsler A and Teichberg VI, *EMBO J* 17:3931-3939, 1998), and induce NMDAR phosphorylation and activation through src-family kinases (Hou X Y et al., *Brain Res* 955:123-132, 2002). The formulation of Fyn-PSD95-NR complexes enhances cell death in brain ischemia, while silencing PSD95 diminishes post-ischemic neuronal cell death (Hou X Y et al., *Neurosci Lett* 385:230-233, 2005).

The src-family kinases that activate NMDAR (Hou X Y et al., *Brain Res* 955:123-132, 2002) are themselves activated by Protein Tyrosine Phosphatases (Lei G et al., *EMBO J* 21:2977-2989, 2002; van Zundert B et al., *Trends Neurosci* 27:428-437, 2004) (PTP), thus the up-regulated PTP-γ (PP1) can be linked to glaucoma and RGC stress. Moreover, protein tyrosine phosphatase activity alters subunit assembly in NMDAR complexes (Ferrani-Kile K and Leslie S W, *Pharmacol Exp Ther* 314:86-93, 2005), and a positive feedback loop exists between PTP-γ (PP1) and NMDAR in numerous (Szatmari E et al., *J Biol Chem* 280(45):37526-35, 2005).

Up-regulated Gzα is a direct interactor and mediator of NMDAR signals. In fact, functional potentiation between α2 macroglobulin/LRP-1 receptor and GTPases has been reported to exacerbate neuronal death (Hashimoto Y et al., *J Neurosci* 20:8401-8409, 2000). Retinal Gzα can also be associated with the activity of several Gi-coupled receptors including the serotonin and opioid receptors (Connor and Christie, 1999). Gzα is expressed highly in neurons (Kelleher K L et al., *Brain Res Dev Brain Res* 107:247-253, 1998) and is retrogradely transported to terminals where it can inhibit neurotrophin signaling and differentiation (Meng J and Casey P J, *J Biol Chem* 277:43417-43424, 2002) through attenuation of RAP-1 activity (Johanson S O et al., *Neurochem Res* 21:779-785, 1996) (see also FIG. 7).

Gene Down-Regulation and RGC Damage

Down-regulation of retinal amphiphysin, a protein which plays a key role in endocytosis and vesicular internalization and transport (Di Paolo G et al., *Neuron* 33:789-804, 2002; Tomizawa K et al., *J Cell Biol* 163:813-824, 2003), could explain compromised axonal transport in glaucoma. Amphiphysin is expressed by RGCs (Hosoya O and Tsutsui K, *Neurosci* 19:2179-2187, 2004). Likewise, down-regulated RKIAS43 is an EST with 98.9% homology to the synaptic vesicle membrane protein VAT-1 (a membrane protein of cholinergic synaptic vesicles), and 80% homology to the vesicle amine transport protein 1; suggesting a role in endocytosis and vesicular function.

Reduced axonal transport has traditionally been explained as a mechanic "physiologic axotomy" of the optic nerve head by compression due to high pressure. The aforementioned data demonstrate that ocular hypertension can mimic physiologic axotomy functionally, by causing a long-lived reduction of expression of vesicular transport proteins that cause retrograde deficits and can lead to RGC death.

Figure 7:
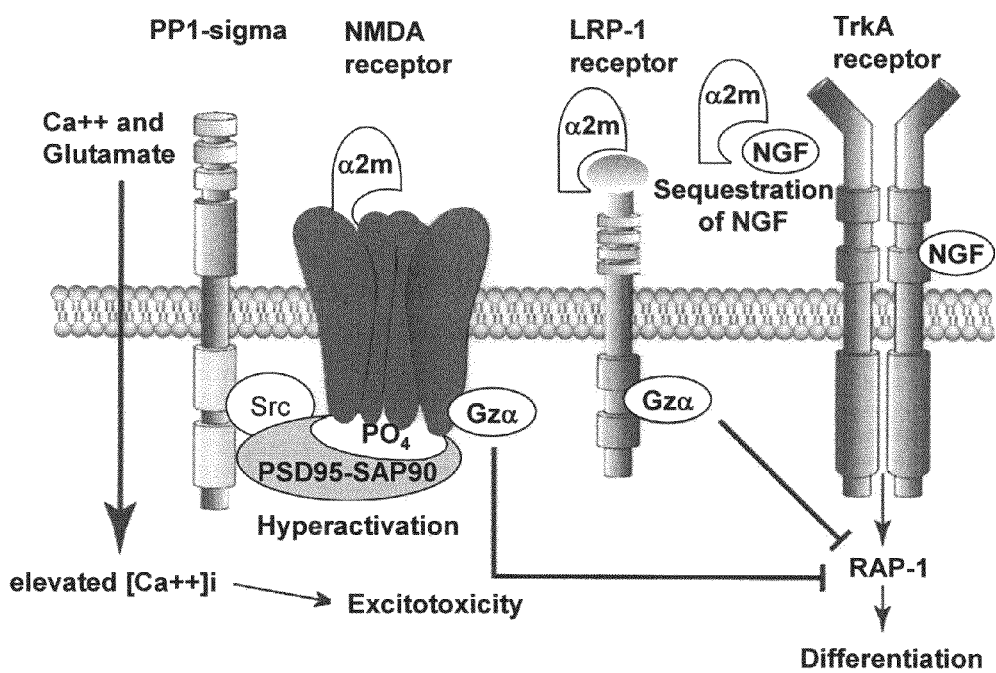
FIG. 7 is a schematic illustrating a model of how IPREGs up-regulated in glaucoma could function together to cause RGC death.

Down-regulated helicase is involved in DNA repair, and lower DNA repair can exacerbate cell death. Specifically relevant to RGC death, helicase is linked functionally to toposiomerases (Howard M T et al., *Proc Natl Acad Sci* 91:12031-12035, 1994), and topoisomerase activity is absolutely required for the transcriptional induction of amphiphysin (Tsutsui K et al., *J Biol Chem* 276:5769-5778, 2001). Hence, down-regulation of amphiphysin as shown in the model in FIG. 7 is consistent with down-regulation of helicase. Lastly, down-regulated Amyloid precursor-like protein 2 is involved in copper homeostasis and possibly in neuroprotection (White A R et al., *J Neurosci* 22:365-376, 2002). Their absence may sensitize RGCs to stress.

Conclusions

The in vivo evidence indicated that ocular hypertension regulates a set of key retinal gene products in a rat model of glaucoma. The expression of a subset of genes was selectively regulated by short-term ocular hypertension and changes were long-lasting even after pharmacological normalization of ocular hypertension. Gene products implicated in RGC death were up-regulated, while gene products involved in RGC maintenance or survival were down-regulated. The soluble protein α2 macroglobulin, one of the retinal gene products markedly up-regulated, was validated as a therapeutic target for the prevention of RGC death in glaucoma.

Example 3

Changes in Intraocular Pressure Regulated Genes after Intraocular α2 Macroglobulin Protein Injection The following experiment was conducted in order to assess changes in gene expression induced in the retina after intraocular injection of α2 macroglobulin protein. 2 μg of α2 macroglobulin protein was intraocularly injected into the right eye of rats (n=3) and the left eye was used as a control. One rat was tested at Day 3, one rat was tested at Day 7 and one rat was tested at Day 14. Retinas were isolated and mRNA was collected. Samples from each of the rats were studied by gene microassays. Retinas were carefully dissected out to insure that only retinal mRNAs were prepared for gene microarray studies. Samples were obtained from control eyes.

RNA Preparation.

Total RNA was isolated from retinal tissue using TRIZOL® (Life Technologies). RNA was then further purified using the RNAEASY® (QIAGEN®). The integrity of the RNA samples was assessed by running aliquots on RNA 6000 Nano LabChip (Agilent) using the 2100 bioanalyzer (Agilent).

Microchip Hybridization.

Probe synthesis, hybridization and scanning were done according to Affymetrix protocol, as a service at the McGill University and Genome Quebec Innovation Centre. For the experiments shown, Rat U34 Genome Arrays (8,700 genes, Affymetrix) were used. Briefly, RNA samples were first converted to double stranded cDNA (T7-(dT)24 primer (Genset)). Then the cDNAs were purified and used to generate the biotinylated cRNA probes (Bioarray High Yield RNA transcript labeling kit (Enzo diagnostics)). An aliquot of the purified cRNA was analyzed on RNA 6000 Nano LabChip (Agilent) to verify the integrity and size distribution. Immediately after hybridization the chip was placed in the Affymetrix GeneChip Fluidics Station 400 (Affymetrix). In total, 10 low-stringency washes (63 SSPE, 0.01% Tween-20, 0.005% Antifoam) and 4 high-stringency washes (100 mM MES, 0.1 M NaCl, 0.01% Tween-20, 50 C) were performed (all reagents from Sigma). The array was then incubated with SAPE® (streptavidin/phycoerythrin stain, Molecular Probes), followed by 10 low stringency washes. The array was incubated with biotinylated anti-streptavidin antibody (Vector Laboratories) and washed again with 15 low stringency washes. Specifically bound probe was detected by placing the array in the Agilent GeneArray scanner 2500 (Affymetrix). The scanned images were analyzed using the Microarray Analysis Suite version 5.0 (Affymetrix).

Data Analysis.

The fold change was analyzed by subtracting data for the control eye from the data on the eye injected with α2 macroglobulin. A fold change of 2 or greater indicates upregulation. A fold of 0.5 to 2 indicates no change. A fold change of 0.5 or less indicates downregulation.

Table 4 shows a summary of 57 genes that were differentially regulated in rat retina after α2 macroglobulin injection at day 3 and day 7 only. Table 5 shows a summary of 24 genes that were differentially regulated in rat retina after α2 macroglobulin injection at day 3, day 7 and day 14. Table 6 shows a grouping of the genes from Table 5 by gene family. α2m in the tables refers to α2 macroglobulin.

Figure 8:
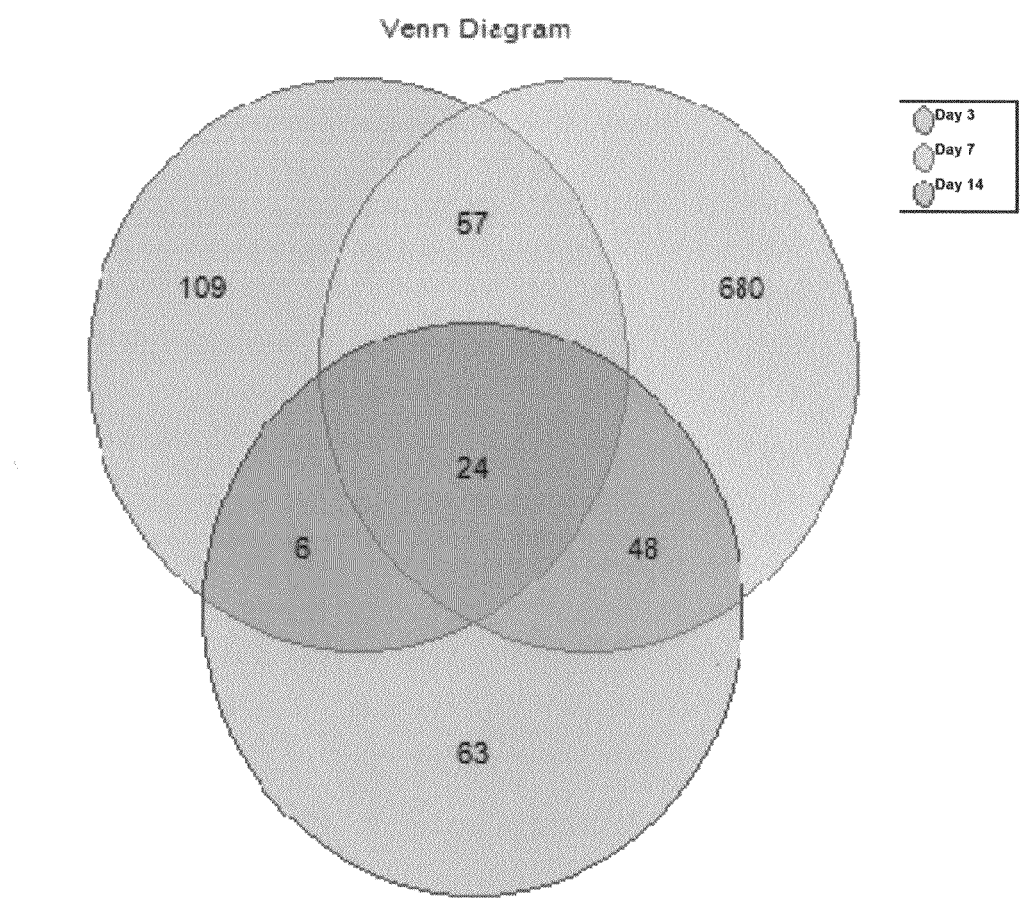
FIG. 8 is a Venn diagram outlining the number of common genes from tables 4 and 5 at Day 3 (pink), Day 7 (blue), and Day 14 (green).

FIG. 8 is a Venn diagram outlining the number of common genes from tables 4 and 5 at Day 3 (pink), Day 7 (blue), and Day 14 (green). There were 196 genes that were identified as differentially regulated in rat retina after α2 macroglobulin intraocular injection (data not shown). Of the 196 genes, 57 genes were identified as differentially regulated in rat retina after α2 macroglobulin injection at day 3 and day 7 only (Table 4) and 24 genes were identified as differentially regulated in rat retina after α2 macroglobulin injection at day 3, day 7 and day 14 (Table 5).

TABLE 4

Summary of 57 Genes Differentially Regulated in Rat Retina after α2 Macroglobulin Injection over 7 days

| Probeset | Accession Number | UniGene ID | Gene Title | Fold Change (α2m vs normal) Day 3 | Fold Change (α2m vs normal) Day 7 |
|---|---|---|---|---|---|
| 1394837_at | BF405797 | — | — | 0.3 | 0.2 |
| 1382211_at | AI602542 | Rn.107412 | Transcribed locus | 0.3 | 4.2 |
| 1380803_at | AI176603 | Rn.8277 | Thyroid hormone receptor interactor 12 | 0.3 | 0.4 |
| 1382193_at | BI294188 | Rn.24858 | similar to RIKEN cDNA 1500009M05 (predicted) | 0.4 | 0.2 |
| 1378518_at | BF394458 | Rn.52785 | Ewing sarcoma breakpoint region 1 | 0.4 | 0.1 |
| 1382510_at | BE105050 | Rn.170932 | Transcribed locus | 0.4 | 0.3 |
| 1383812_at | BG373436 | Rn.40868 | similar to Phakinin (Beaded filament structural protein 2) | 0.4 | 2.7 |
| 1392675_at | AI044784 | Rn.166013 | Transcribed locus | 0.4 | 0.3 |
| 1370964_at | BF283456 | Rn.5078 | argininosuccinate synthetase | 0.4 | 2.4 |
| 1390657_at | BI291389 | Rn.198543 | Similar to expressed sequence AV312086 (predicted) | 0.4 | 0.3 |
| 1395390_at | BM384238 | Rn.26826 | Transcribed locus | 0.4 | 4.1 |
| 1385108_at | AW524173 | Rn.149172 | Similar to hypothetical protein D630010C10 | 0.4 | 0.2 |

TABLE 4-continued

Summary of 57 Genes Differentially Regulated in Rat Retina after α2 Macroglobulin Injection over 7 days

| Probeset | Accession Number | UniGene ID | Gene Title | Fold Change (α2m vs normal) Day 3 | Fold Change (α2m vs normal) Day 7 |
|---|---|---|---|---|---|
| 1388746_at | BI297836 | Rn.176515 | similar to serine (or cysteine) proteinase inhibitor | 0.4 | 2.6 |
| 1392282_at | BE114642 | Rn.6834 | ADP-ribosylation factor guanine nucleotide-exchange factor 1 | 0.5 | 0.3 |
| 1368584_a_at | NM_053878 | Rn.10134 | complexin 2 | 0.5 | 0.2 |
| 1375309_at | BI296631 | Rn.8515 | High density lipoprotein binding protein | 0.5 | 0.5 |
| 1391315_at | BM386843 | Rn.58464 | similar to mKIAA1450 protein (predicted) | 0.5 | 0.2 |
| 1382862_at | BE119506 | Rn.139546 | ash1 (absent, small, or homeotic)-like (Drosophila) (predicted) | 0.5 | 0.2 |
| 1398217_at | BE108367 | Rn.51461 | similar to FRBZ1 protein (FRBZ1) (predicted) | 0.5 | 0.2 |
| 1386933_at | NM_134418 | Rn.11223 | glycoprotein 2 (zymogen granule membrane) | 0.5 | 2.1 |
| 1385552_at | BG668477 | Rn.176691 | Transcribed locus | 0.5 | 0.3 |
| 1384241_at | BE096332 | Rn.23610 | crystallin, gamma N (predicted) | 0.5 | 3.9 |
| 1369003_at | NM_031800 | Rn.146589 | death effector domain-containing | 0.5 | 0.4 |
| 1386212_at | AI639523 | Rn.44157 | spectrin alpha 1 | 0.5 | 2.1 |
| 1369715_at | M95763 | Rn.10545 | solute carrier family 6 (neurotransmitter transporter, GABA | 0.5 | 0.4 |
| 1368493_at | NM_053771 | Rn.9688 | lens intrinsic membrane protein 2 | 0.5 | 2.5 |
| 1395129_at | BE107340 | Rn.51160.1 | — | 0.5 | 0.3 |
| 1385852_at | BF566908 | Rn.108128 | CREB binding protein | 0.5 | 0.4 |
| 1376087_at | BM386653 | Rn.28889 | similar to RIKEN cDNA 1300010M03 (predicted) | 0.5 | 0.4 |
| 1389868_at | AA850780 | Rn.164112 | similar to RCK (predicted) | 0.5 | 0.2 |
| 1390813_at | AI236624 | Rn.43808 | similar to RNA-binding protein Musashi2-S (predicted) | 0.5 | 0.2 |
| 1391152_at | AI412781 | Rn.78670 | similar to RIKEN cDNA 4930555G01 (predicted) | 2.0 | 5.6 |
| 1375170_at | BG378926 | Rn.104930 | S100 calcium binding protein A11 (calizzarin) | 2.0 | 4.5 |
| 1392894_at | AI716194 | Rn.64635 | fibrinogen-like 2 | 2.1 | 2.1 |
| 1368332_at | NM_133624 | Rn.25736 | guanylate nucleotide binding protein 2 | 2.2 | 2.1 |
| 1370892_at | BI285347 | Rn.81052 | complement component 4a | 2.2 | 2.3 |
| 1392155_at | AW523955 | Rn.147947 | Transcribed locus | 2.4 | 16.6 |
| 1397883_at | H33845 | Rn.153398 | Transcribed locus | 2.4 | 17.0 |

TABLE 4-continued

Summary of 57 Genes Differentially Regulated in Rat Retina after α2 Macroglobulin Injection over 7 days

| Probeset | Accession Number | UniGene ID | Gene Title | Fold Change (α2m vs normal) Day 3 | Fold Change (α2m vs normal) Day 7 |
|---|---|---|---|---|---|
| 1386925_at | NM_019289 | Rn.2090 | actin related protein 2/3 complex, subunit 1B | 2.7 | 2.0 |
| 1372254_at | AW915763 | Rn.100285 | serine (or cysteine) peptidase inhibitor, clade G, member 1 | 3.0 | 3.3 |
| 1370959_at | BI275716 | Rn.3247 | procollagen, type III, alpha 1 | 3.7 | 3.4 |
| 1370956_at | BM390253 | Rn.106103 | decorin | 3.7 | 12.6 |
| 1368187_at | NM_133298 | Rn.13778 | glycoprotein (transmembrane) nmb | 3.9 | 7.4 |
| 1389470_at | AI639117 | Rn.109148 | complement factor B | 3.9 | 3.3 |
| 1370383_s_at | BI279526 | — | RT1 class II, locus Db1 | 4.9 | 3.5 |
| 1390510_at | BI294706 | Rn.17885 | membrane-spanning 4-domains, subfamily A, member 6B | 5.1 | 2.1 |
| 1372013_at | BG380285 | Rn.22087 | interferon induced transmembrane protein 1 (predicted) | 5.8 | 4.2 |
| 1387893_at | D88250 | Rn.195839 | complement component 1, s subcomponent | 6.0 | 3.6 |
| 1371033_at | AI715202 | Rn.33311 | RT1 class II, locus Bb | 6.8 | 5.2 |
| 1373349_at | AI764437 | — | similar to keratin complex 2, basic, gene 6a | 7.3 | 0.4 |
| 1370154_at | L12458 | Rn.2283 | lysozyme | 7.8 | 2.8 |
| 1370822_at | AF307302 | Rn.25717 | RT1 class II, locus Ba | 8.3 | 4.5 |
| 1368000_at | NM_016994 | Rn.11378 | complement component 3 | 8.4 | 2.1 |
| 1371079_at | X73371 | Rn.33323 | Fc receptor, IgG, low affinity IIb | 9.4 | 2.1 |
| 1367679_at | NM_013069 | Rn.33804 | CD74 antigen | 10.1 | 6.5 |
| 1370883_at | Y00480 | Rn.103146 | RT1 class II, locus Da | 16.1 | 11.3 |
| 1373010_at | BG372059 | Rn.136641 | LOC361776 | 20.1 | 0.5 |

TABLE 5

Summary of 24 Genes Differentially Regulated in Rat Retina after α2 Macroglobulin Injection over 14 days

| Probeset | Accession Number | UniGene ID | Gene Title | Fold Change (α2m vs normal) Day 3 | Fold Change (α2m vs normal) Day 7 | Fold Change (α2m vs normal) Day 14 |
|---|---|---|---|---|---|---|
| 1372439_at | AI176393 | Rn.53801 | procollagen, type IV, alpha 1 | 0.3 | 17.5 | 2.4 |
| 1373245_at | BE111752 | Rn.53801 | procollagen, type IV, alpha 1 | 0.3 | 13.2 | 2.3 |
| 1386947_at | NM_031334 | Rn.1303 | cadherin 1 | 0.4 | 9.6 | 2.4 |
| 1367990_at | NM_031690 | Rn.19693 | crystallin, beta B3 | 0.4 | 4.2 | 2.0 |
| 1382809_at | AW921084 | Rn.28931 | cold inducible RNA binding protein | 0.4 | 0.1 | 2.2 |

TABLE 5-continued

Summary of 24 Genes Differentially Regulated in Rat Retina after α2 Macroglobulin Injection over 14 days

| Probeset | Accession Number | UniGene ID | Gene Title | Fold Change (α2m vs normal) Day 3 | Fold Change (α2m vs normal) Day 7 | Fold Change (α2m vs normal) Day 14 |
|---|---|---|---|---|---|---|
| 1390398_at | AI179372 | Rn.88925 | Bone morphogenetic protein receptor, type 1A | 0.4 | 0.2 | 2.6 |
| 1367684_at | NM_012937 | Rn.10350 | crystallin, beta B2 | 0.4 | 3.7 | 2.2 |
| 1381100_at | BE108751 | Rn.199529 | Transcribed locus | 0.4 | 0.3 | 5.4 |
| 1386936_at | NM_057187 | Rn.118963 | Exosome component 8 (predicted) | 0.4 | 4.3 | 2.4 |
| 1393766_at | AI112375 | — | — | 0.4 | 0.3 | 3.6 |
| 1370797_at | L13207 | Rn.92407 | forkhead box E3 | 0.4 | 2.9 | 2.2 |
| 1382368_at | AA943075 | Rn.148297 | Transcribed locus | 0.4 | 0.2 | 2.7 |
| 1384681_at | AI713014 | Rn.41044 | FERM domain containing 4B | 0.5 | 0.2 | 2.3 |
| 1370072_at | NM_012608 | Rn.33598 | membrane metallo endopeptidase | 0.5 | 5.3 | 2.2 |
| 1391757_at | AA926072 | Rn.25328 | Transcribed locus | 0.5 | 0.2 | 2.0 |
| 1388435_at | BG373193 | Rn.198271 | similar to Beta crystallin S (Gamma crystallin S) | 0.5 | 2.8 | 2.9 |
| 1394756_at | AA955494 | Rn.28431 | Similar to CG10084-PA | 0.5 | 0.3 | 2.4 |
| 1388385_at | BG371710 | — | crystallin, beta A2 | 0.5 | 3.6 | 2.0 |
| 1397412_at | BE107094 | Rn.107173 | Similar to NICE-3 | 0.5 | 0.4 | 2.0 |
| 1368778_at | NM_017206 | Rn.9968 | solute carrier family 6 | 0.5 | 0.2 | 2.3 |
| 1389986_at | AI008409 | Rn.119131 | CDNA clone IMAGE: 7321089 | 0.5 | 0.3 | 2.9 |
| 1369985_at | NM_012936 | Rn.10602 | crystallin, beta B1 | 0.5 | 3.4 | 2.0 |
| 1384014_at | BE109675 | Rn.166585 | Transcribed locus | 0.5 | 4.2 | 2.0 |
| 1367749_at | NM_031050 | Rn.3087 | lumican | 6.1 | 4.1 | 0.4 |

TABLE 6

Summary of Gene Families Differentially Regulated in Rat Retina after α2 Macroglobulin Injection over 7 and/or 14 days

| Probeset | Accession Number | UniGene ID | Gene Title | Fold Change (α2m vs normal) Day 3 | Fold Change (α2m vs normal) Day 7 | Fold Change (α2m vs normal) Day 14 |
|---|---|---|---|---|---|---|
| 1387893_at | D88250 | Rn.195839 | complement component 1, s subcomponent | 6.0 | 3.6 | |
| 1368000_at | NM_016994 | Rn.11378 | complement component 3 | 8.4 | 2.1 | |
| 1370892_at | BI285347 | Rn.81052 | complement component 4a | 2.2 | 2.3 | |
| 1389470_at | AI639117 | Rn.109148 | complement factor B | 3.9 | 3.3 | |
| 1370822_at | AF307302 | Rn.25717 | RT1 class II, locus Ba | 8.3 | 4.5 | |
| 1371033_at | AI715202 | Rn.33311 | RT1 class II, locus Bb | 6.8 | 5.2 | |

TABLE 6-continued

Summary of Gene Families Differentially Regulated in Rat Retina after α2 Macroglobulin Injection over 7 and/or 14 days

| Probeset | Accession Number | UniGene ID | Gene Title | Fold Change (α2m vs normal) Day 3 | Fold Change (α2m vs normal) Day 7 | Fold Change (α2m vs normal) Day 14 |
|---|---|---|---|---|---|---|
| 1370883_at | Y00480 | Rn.103146 | RT1 class II, locus Da | 16.1 | 11.3 | |
| 1370383_s_at | BI279526 | — | RT1 class II, locus Db1 | 4.9 | 3.5 | |
| 1384241_at | BE096332 | Rn.23610 | crystallin, gamma N (predicted) | 0.5 | 3.9 | |
| 1388385_at | BG371710 | — | crystallin, beta A2 | 0.5 | 3.6 | 2.0 |
| 1369985_at | NM_012936 | Rn.10602 | crystallin, beta B1 | 0.5 | 3.4 | 2.0 |
| 1367684_at | NM_012937 | Rn.10350 | crystallin, beta B2 | 0.4 | 3.7 | 2.2 |
| 1367990_at | NM_031690 | Rn.19693 | crystallin, beta B3 | 0.4 | 4.2 | 2.0 |
| 1370959_at | BI275716 | Rn.3247 | procollagen, type III, alpha 1 | 3.7 | 3.4 | |
| 1372439_at | AI176393 | Rn.53801 | procollagen, type IV, alpha 1 | 0.3 | 17.5 | 2.4 |
| 1373245_at | BE111752 | Rn.53801 | procollagen, type IV, alpha 1 | 0.3 | 13.2 | 2.3 |
| 1369715_at | M95763 | Rn.10545 | solute carrier family 6 (neurotransmitter transporter, GABA), | 0.5 | 0.4 | |
| 1368778_at | NM_017206 | Rn.9968 | solute carrier family 6 (neurotransmitter transporter, taurine) | 0.5 | 0.2 | 2.3 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating glaucoma by reducing retinal ganglion cell (RGC) death mediated by high intraocular pressure (IOP) in a mammal in need thereof comprising administering to the mammal a composition comprising an effective amount of an anti-α2 macroglobulin neutralizing antibody.

2. The method of claim 1 wherein the composition is administered by at least one method selected from the group consisting of intraocular injection, topical conjunctival application, topical corneal application, and eye insert.

3. The method of claim 1 wherein the α2 macroglobulin protein activity is inhibited by antagonizing α2 macroglobulin protein receptors.

4. The method of claim 3 further comprising administering one or more intraocular pressure-normalizing drugs.

5. The method of claim 4 wherein the one or more intraocular pressure-normalizing drugs are selected from the group consisting of non-selective-adrenoceptor blockers, selective-adrenoceptor blockers, prostaglandins, carbonic anhydrase inhibitors, adrenergic agonists and miotics.

6. The method of claim 5 wherein the intraocular pressure-normalizing drug administered is betaxolol.

7. A method of inhibiting chronic ocular degeneration caused by increased intraocular pressure or α2 macroglobulin over-expression in a mammal in need thereof comprising administering to the mammal a composition comprising an effective amount of an anti-α2 macroglobulin neutralizing antibody.

8. The method of claim 7 further comprising administering one or more intraocular pressure-normalizing drugs.

9. The method of claim 7 wherein the composition is administered by at least one method selected from the group consisting of intraocular injection, topical conjunctival application, topical corneal application, and eye insert.

10. The method of claim 7 wherein the α2 macroglobulin protein activity is inhibited by antagonizing α2 macroglobulin protein receptors.

11. The method of claim 8 wherein the one or more intraocular pressure-normalizing drugs are selected from the group consisting of non-selective-adrenoceptor blockers, selective-adrenoceptor blockers, prostaglandins, carbonic anhydrase inhibitors, adrenergic agonists and miotics.

12. The method of claim 11 wherein the intraocular pressure-normalizing drug administered is betaxolol.

* * * * *